US012759998B2

(12) United States Patent
Igawa

(10) Patent No.: US 12,759,998 B2
(45) Date of Patent: Oct. 13, 2026

(54) ORGANIC COMPOUND AND ELECTROCHROMIC ELEMENT

(71) Applicant: CANON KABUSHIKI KAISHA, Tokyo (JP)

(72) Inventor: Satoshi Igawa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 331 days.

(21) Appl. No.: 18/439,430

(22) Filed: Feb. 12, 2024

(65) Prior Publication Data

US 2024/0294490 A1 Sep. 5, 2024

(30) Foreign Application Priority Data

Feb. 17, 2023 (JP) ................................ 2023-023495
Oct. 26, 2023 (JP) ................................ 2023-183964

(51) Int. Cl.
*C07D 401/04* (2006.01)
*C09K 9/02* (2006.01)
*G02F 1/1516* (2019.01)
*G02F 1/155* (2006.01)

(52) U.S. Cl.
CPC .............. *C07D 401/04* (2013.01); *C09K 9/02* (2013.01); *G02F 1/1516* (2019.01); *G02F 1/155* (2013.01); *C09K 2211/1018* (2013.01)

(58) Field of Classification Search
CPC ............................... C07D 401/04; C09K 9/02; C09K 2211/1018; G02F 1/155; G02F 1/1516
See application file for complete search history.

(56) References Cited

U.S. PATENT DOCUMENTS

2021/0109415 A1* 4/2021 Igawa ...................... C09K 9/02

FOREIGN PATENT DOCUMENTS

JP 2020152708 A 9/2020
JP 2022070461 A * 5/2022 ........... C07D 471/06

* cited by examiner

*Primary Examiner* — Bijan Ahvazi
(74) *Attorney, Agent, or Firm* — Canon.U.S.A., Inc. IP Division

(57) ABSTRACT

An organic compound represented by formula (1) is provided:

(1)

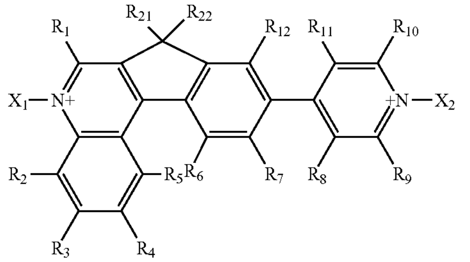

In formula (1), $X_1$ and $X_2$ are each independently selected from the group consisting of alkyl groups, aryl groups, and aralkyl groups. $R_1$ to $R_{12}$ are each independently selected from the group consisting of a hydrogen atom, a deuterium atom, halogen atoms, alkyl groups, alkoxy groups, and aryl groups. $R_{21}$ and $R_{22}$ are each independently selected from the group consisting of a hydrogen atom, a deuterium atom, alkyl groups, and aryl groups.

20 Claims, 5 Drawing Sheets

ORGANIC COMPOUND AND ELECTROCHROMIC ELEMENT

BACKGROUND OF THE INVENTION

Field of the Invention

The present disclosure relates to an organic compound and an electrochromic element using the organic compound.

Description of the Related Art

An electrochromic (hereinafter also abbreviated to EC) element includes a pair of electrodes and an EC layer disposed between the pair of electrodes. The EC element can adjust the amount of light passing through the EC layer when voltage is applied to the pair of electrodes. In other words, the EC element can control its light transmittance.

EC materials are substances whose optical absorption properties (e.g., coloring state and light transmittance) are varied by electrochemical redox reaction. Various materials, including inorganic, low-molecular-weight organic, and polymer materials, are known as EC materials.

Such EC materials have been used in EC elements applied to dimming mirrors in automobiles, electronic papers, and other devices. These devices take advantage of a characteristic of EC materials that a variety of color tones can be displayed depending on the selection of the material. Developing materials for various color tones is desired for using EC elements. For example, for application to full-color display devices or the like, materials to color cyan, magenta, or yellow are used. For a wider range of applications, coloring materials for various colors and tones are required.

Japanese Patent Laid-Open No. 2020-152708 (hereinafter abbreviated to PTL 1) discloses a cathodic EC compound that exhibits an absorption peak at around 500 nm.

However, this compound alone is not sufficient for a wide range of applications of EC elements.

SUMMARY OF THE INVENTION

The present disclosure provides an organic compound that can absorb longer wavelength light.

The organic compound is represented by formula (1):

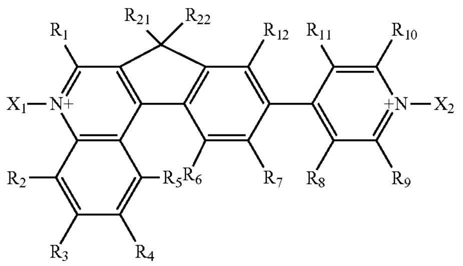

(1)

In formula (1), $X_1$ and $X_2$ are each independently selected from the group consisting of substituted or unsubstituted alkyl groups, substituted or unsubstituted aryl groups, and substituted or unsubstituted aralkyl groups.

$R_1$ to $R_{12}$ are each independently selected from the group consisting of a hydrogen atom, a deuterium atom, halogen atoms, substituted or unsubstituted alkyl groups, substituted or unsubstituted alkoxy groups, and substituted or unsubstituted aryl groups.

$R_{21}$ and $R_{22}$ are each independently selected from the group consisting of a hydrogen atom, a deuterium atom, substituted or unsubstituted alkyl groups, and substituted or unsubstituted aryl groups.

Further features of the present disclosure will become apparent from the following description of exemplary embodiments with reference to the attached drawings.

DESCRIPTION OF THE EMBODIMENTS

Figure 1:
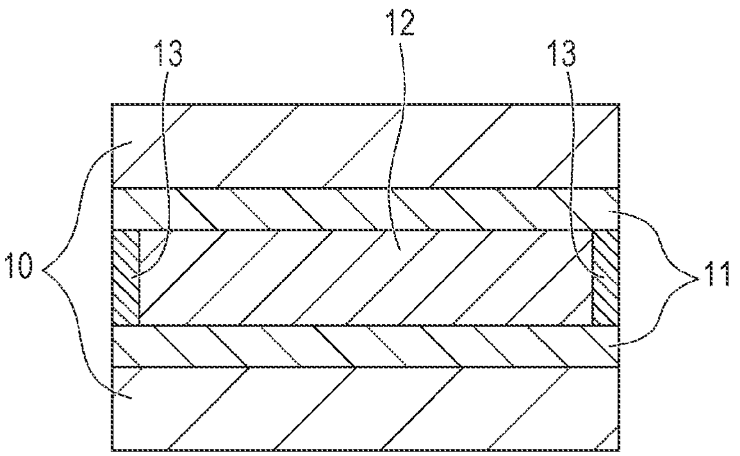
FIG. 1 is a schematic sectional view of an electrochromic element according to an embodiment.

In the description herein, halogen atoms include, but are not limited to, fluorine, chlorine, bromine, and iodine.

The alkyl groups may have 1 to 20 carbon atoms, for example, 1 to 8 carbon atoms, and may be substituted, unsubstituted, or cyclic. Examples of alkyl groups include, but are not limited to, methyl, ethyl, n-propyl, isopropyl, n-butyl, tert-butyl, sec-butyl, octyl, cyclohexyl, 1-adamantyl, and 2-adamantyl. Substituents that the alkyl groups may have include, but are not limited to, halogen atoms, ester groups, and the cyano group. Also, a halogen atom, for example, a fluorine atom, may substitute for a hydrogen atom of the alkyl group. An ester or a cyano group may substitute for a carbon atom in the alkyl group.

The aryl groups may have 6 to 20 carbon atoms. Examples include, but are not limited to, phenyl, biphenyl, terphenyl, fluorenyl, naphthyl, fluoranthenyl, anthryl, phenanthryl, pyrenyl, tetracenyl, pentacenyl, triphenylenyl, and perylenyl. The aryl groups may have at least one or more substituents selected from halogen atoms, alkyl groups having 1 to 8 carbon atoms, and alkoxy groups having 1 to 8 carbon atoms. Also, a halogen atom, for example, a fluorine atom, may substitute for a hydrogen atom of the alkyl or alkoxy group.

The alkoxy group may have 1 to 10 carbon atoms. Examples of such alkoxy groups include, but are not limited to, methoxy, ethoxy, propoxy, isopropoxy, butoxy, tert-butoxy, 2-ethyl-octyloxy, and benzyloxy.

An aryloxy group may be a substituent, and examples include, but are not limited to, phenoxy.

The aralkyl group may have 7 to 20 carbon atoms. Examples include, but are not limited to, benzyl and phenethyl. The aralkyl group may have one or more substituents, such as alkyl groups with 1 to 8 carbon atoms or alkoxy groups with 1 to 8 carbon atoms. A halogen atom, for example, a fluorine atom, may substitute for a hydrogen atom of the alkyl or alkoxy group.

Examples of ester groups include, but are not limited to, carboxylate ester groups, sulfonic ester groups, and phosphonate ester groups.

The term cathodic EC compound used herein refers to an organic compound that colors when reduced. The term anodic EC compound refers to an organic compound that colors when oxidized.

Also, in the description herein, "coloring" implies that the transmittance of a specific wavelength decreases.

An organic compound that colors when reduced refers to an organic compound whose visible light transmittance in reduction is lower than in oxidation. In contrast, an organic compound that colors when oxidized refers to an organic compound whose visible light transmittance in oxidation is lower than in reduction. The transmittance has to vary at any wavelength in the visible region but need not vary throughout the entire visible region.

(1) Organic Compound

The organic compound disclosed herein will first be described.

The organic compound disclosed herein (hereinafter also referred to as the present organic compound) is represented by the following formula (1) and is electrochromic. Accordingly, the organic compound may also be referred to as the EC compound. The present organic compound colors when reduced.

(1)

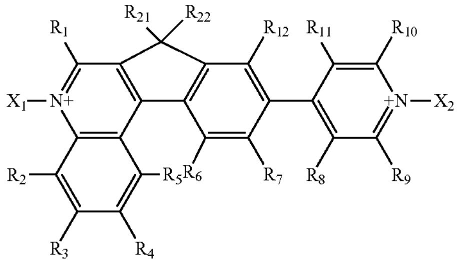

In formula (1), $X_1$ and $X_2$ are each independently selected from the group consisting of substituted or unsubstituted alkyl groups, substituted or unsubstituted aryl groups, and substituted or unsubstituted aralkyl groups. $X_1$ and $X_2$ may be alkyl groups with 1 to 8 carbon atoms, aryl groups with 6 to 10 carbon atoms, or aralkyl groups with 6 to 10 carbon atoms and, in some embodiments, may be alkyl with 1 to 8 carbon atoms or aryl with 6 to 10 carbon atoms, particularly phenyl. $X_1$ and $X_2$ may have different structures but, in some embodiments, may have the same structure because of ease of synthesis.

When $X_1$ and $X_2$ are alkyl groups, the alkyl groups may have adsorbable groups or their acid ester groups to be adsorbed on an electrode. The electrode may be porous. Examples of adsorbable groups and their acid ester groups include carboxyl and carboxylate ester groups, sulfonic and sulfonic ester groups, phosphonate and phosphonate ester groups, and trialkoxysilyl groups. $X_1$ and $X_2$ having adsorbable groups or their acid ester groups may have carboxyl, carboxylate ester, sulfonic, phosphonate, or phosphonate ester groups.

In an embodiment, an alkyl group of the present organic compound may have a polymerizable functional group at the end to make the compound polymeric. Specific examples of the polymerizable functional group include acrylic, methacrylic, and hydroxy groups. Also, an alkyl group may have an ionic group, such as pyridinium or quinolinium, at the end to increase the solubility in organic solvent.

When $X_1$ and $X_2$ are aralkyl or aryl having alkyl or alkoxy as a substituent, the end of the substituent may have an adsorbable group or its acid ester to be adsorbed on the electrode or a polymerizable functional group to make the compound polymeric. Also, the substituent, alkyl or alkoxy, may have an ionic group to increase the solubility in organic solvent. Examples of the adsorbable group and its acid ester and the ionic group are the same as cited above. $X_1$ and $X_2$ having an adsorbable group, its acid ester group, or an ionic group may have a carboxylate ester group, phosphonate group, or pyridinium group.

$R_1$ to $R_{12}$ are each independently selected from the group consisting of a hydrogen atom, a deuterium atom, halogen atoms, substituted or unsubstituted alkyl groups, substituted or unsubstituted alkoxy groups, and substituted or unsubstituted aryl groups. $R_1$ to $R_{12}$ may be hydrogen atoms, halogen atom atoms, aryl groups with 6 to 10 carbon atoms, or alkoxy groups with 1 to 4 carbon atoms and are, in some embodiments, hydrogen atoms.

$R_{21}$ and $R_{22}$ are each independently selected from the group consisting of a hydrogen atom, a deuterium atom, substituted or unsubstituted alkyl groups, and substituted or unsubstituted aryl groups. $R_{21}$ and $R_{22}$ may be hydrogen atoms or alkyl groups with 1 to 4 carbon atoms and are, in some embodiments, methyl groups.

In an embodiment, the organic compound may contain monovalent anions $A_1^-$ and $A_2^-$ as counter ions. $A_1^-$ and $A_2^-$ are each independently selected from anions such as $PF_6^-$, $ClO_4^-$, $BF_4^-$, $AsF_6^-$, $SbF_6^-$, $CF_3SO_3^-$, and $(CF_3SO_2)_2N^-$ and halogen anions, such as $Br^-$, $Cl^-$, and $I^-$. For example, $A_1^-$ and $A_2^-$ may be $Cl^-$, $Br^-$, $I^-$, $BF_4^-$, $PF_6^-$, $ClO_4^-$, $CF_3SO_3^-$, or $(CF_3SO_2)_2N^-$ and, in some embodiments, $BF_4^-$ or $PF_6^-$. $A_1^-$ and $A_2^-$ may be the same or different but are, in some embodiments, the same anions because of ease of synthesis.

Specifically, the present organic compound may be represented by formula (2):

(2)

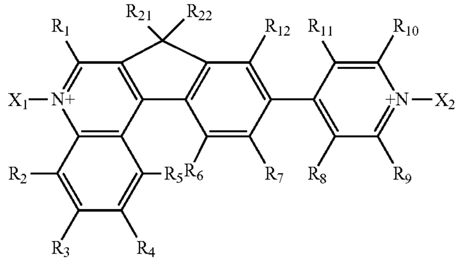

$A_1^-A_2^-$

In formula (2), $X_1$ and $X_2$ are each independently selected from the group consisting of substituted or unsubstituted alkyl groups, substituted or unsubstituted aryl groups, and substituted or unsubstituted aralkyl groups.

$R_1$ to $R_{12}$ are each independently selected from the group consisting of a hydrogen atom, a deuterium atom, halogen atoms, substituted or unsubstituted alkyl groups, substituted or unsubstituted alkoxy groups, and substituted or unsubstituted aryl groups.

$R_{21}$ and $R_{22}$ are each independently selected from the group consisting of a hydrogen atom, a deuterium atom, substituted or unsubstituted alkyl groups, and substituted or unsubstituted aryl groups.

$A_1^-$ and $A_2^-$ are each a monovalent anion.

The organic compound having the skeleton represented by formula (1) and the organic compound represented by formula (2) have the following characteristics:

(1-1) The conjugation length of the molecule is elongated, enabling the molecule to absorb longer wavelength light.

(1-2) A benzene ring is fused at a specific position to enhance the durability.

These characteristics will now be described in detail.

(1-1) The Conjugation Length of the Molecule is Elongated, Enabling the Molecule to Absorb Longer Wavelength Light.

The present organic compound has the skeleton represented by formula (1) or is represented by formula (2). Accordingly, the conjugation length of the present organic compound can elongate more than that of the organic compound of PTL 1, enabling the molecule to absorb longer wavelength light.

The absorption wavelengths of the present organic compounds and PTL 1 are presented in the following Table 1. The absorption wavelengths were determined by UV-visible absorption spectrum measurements. The light source was a DH-2000S light source using deuterium and halogen lamps manufactured by Ocean Optics, Inc.

TABLE 1

| | Structural formula | Absorption wavelength |
|---|---|---|
| Exemplified Compound A-13 | 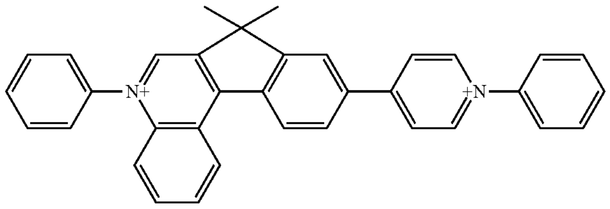 2$PF_6^-$ | 570 nm |
| Compound 1-a | 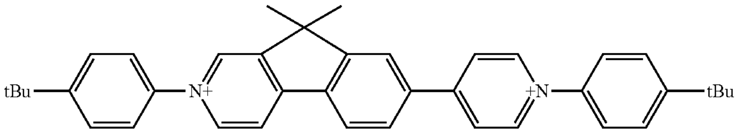 2$PF_6$ | 536 nm |

In Table 1, Exemplified Compound A-13 is an organic compound disclosed herein, and Compound 1-a is an organic compound disclosed in PTL 1. While the absorption wavelength of Compound 1-a was 536 nm, the absorption wavelength of Exemplified Compound A-13 was 570 nm. Thus, the present organic compound can absorb longer wavelength light than the organic compound of PTL 1.

The present inventors focus on the conjugation length of molecules as a factor that enables the present organic compound to absorb longer wavelength light. The organic compound disclosed in PTL 1 has a structure in which an azafluorene skeleton is bound to a pyridine skeleton. In contrast, the present organic compound has a structure in which an azabenzofluorene skeleton formed by fusing benzene with an azafluorene skeleton is bound to a pyridine skeleton. The conjugation length of the present organic compound, which contains more benzene rings than the organic compound of PTL 1, elongates more than the organic compound of PTL 1. As a result, the present organic compound can absorb longer wavelength light.

(1-2) A Benzene Ring is Fused at a Specific Position to Enhance the Durability.

The present inventors have found that the fusion of benzene at a specific position of Compound 1-a enhances durability.

The fusion of benzene with Compound 1-a can form skeletons represented by the following formulas (3) and (4):

(3)

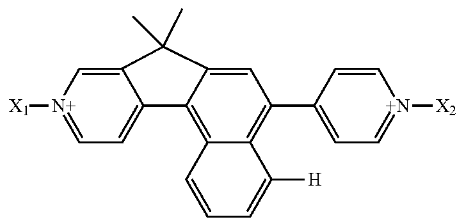

(4)

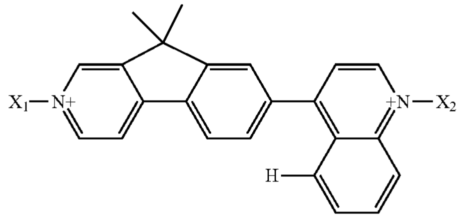

When organic compounds having these skeletons are radicalized, the molecular structures of two rings containing imine are expected to be planarized. When organic compounds having a large steric hindrance return from the radical state to the ground state, the steric hindrance may hinder the molecule from returning to the original structure. At this time, the compound deteriorates in terms of an EC compound. More specifically, when organic compounds having the skeletons represented by formulas (3) and (4) are radicalized, the steric hindrance between the hydrogen atom at the peri-position (H in the formula) and the hydrogen atom in the 3-position of pyridine or the 6-position of azafluorene increases. Accordingly, in the organic compounds having the skeletons represented by formulas (3) and (4), the hydrogen at the peri-position of the fused benzene may reduce the durability.

In contrast, in the skeleton represented by formula (1), the hydrogen at the peri-position of the fused benzene lies at a position unlikely to form a steric hindrance with the adjacent pyridine ring. Thus, the present organic compound is superior in durability to the compounds represented by formulas (3) and (4).

Additionally, the present organic compound may have the following characteristics.

(1-3) The Present Organic Compound Contains Substituents Increasing the Solubility.

The present organic compound may be dissolved in a solvent before use, as described later. Therefore, in some embodiments, the present organic compound has substituents increasing the solubility.

In some embodiments, the present organic compound has bulky substituents from the viewpoint of increasing the solubility of the compound. Examples of bulky substituents include alkyl groups with 1 to 7 carbon atoms, alkoxy groups with 1 to 7 carbon atoms, aryl groups with 6 to 18 carbon atoms, and aryloxy groups with 6 to 10 carbon atoms. More specifically, the bulky substituents may be isopropyl, tert-butyl, methoxy, ethoxy, isopropoxy, tert-butoxy, terphenyl, or phenoxy.

The present organic compound may be produced in any process without particular limitation and may be, for example, in the following processes. For the organic compound in which at least either $X_1$ or $X_2$ is alkyl or aralkyl, an organic compound represented by the following formula (5) is reacted with a halide in a given solvent. Then, the resulting compound is subjected to an anion exchange reaction with a salt containing a desired anion in a given solvent to yield the desired organic compound.

For the organic compound in which at least either $X_1$ or $X_2$ is aryl, an organic compound represented by the following formula (5) is reacted with a hypervalent iodine compound in a given solvent. Then, the resulting compound is subjected to an anion exchange reaction with a salt containing an anion in a given solvent to yield the desired organic compound. Only the imine on one side may be reacted by selecting the solvent and reaction temperature. Repeating reactions enables different substituents to be introduced to the two imine moieties.

(5)

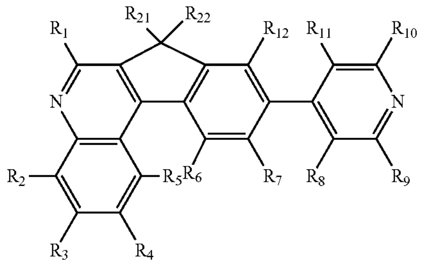

The organic compound represented by formula (5) may be produced in any process without particular limitation and may be, for example, in the following process. In the following synthesis process, $R_1$ to $R_{12}$ and $R_{21}$ and $R_{22}$ represent hydrogen atoms or substituents as in formulas (1) and (2), in which R represents alkyl groups and X represents halogen atoms.

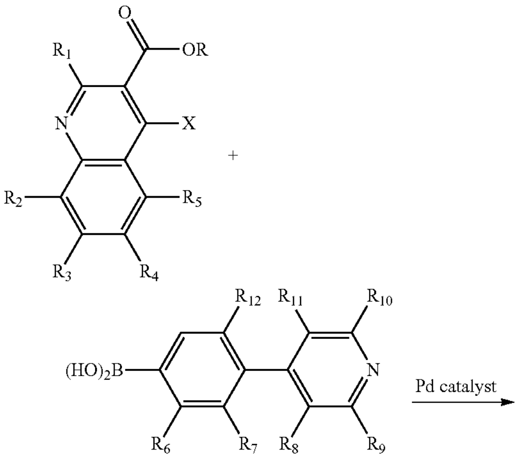

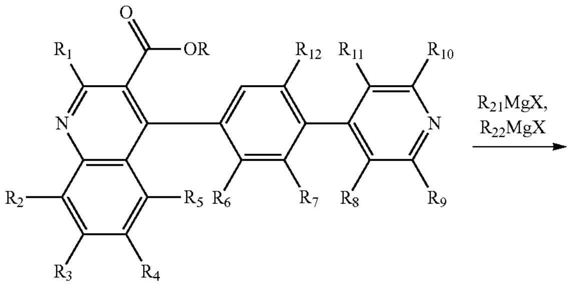

Intermediate 1

-continued

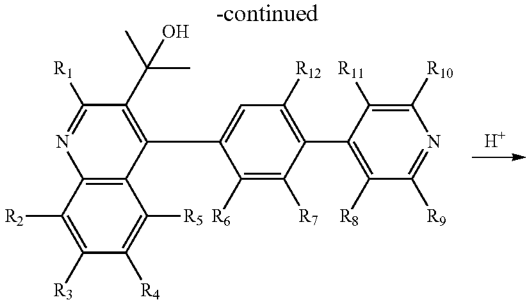

Intermediate 2

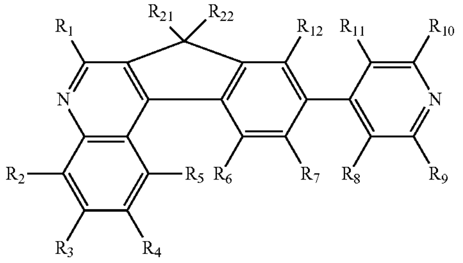

(5)

Intermediate 1 can be synthesized by coupling an alkyl 4-halogenoquinoline-3-carboxylate derivative with a 4-(4'-pyridyl)phenylboronic acid derivative. Intermediate 2 can be synthesized by reacting a Grignard reagent with Intermediate 1. The organic compound represented by formula (5) can be synthesized by cyclizing Intermediate 2 in the presence of acid.

Specific structural formulas of the present organic compound are presented below, but the present organic compound is not limited to the following.

A-1

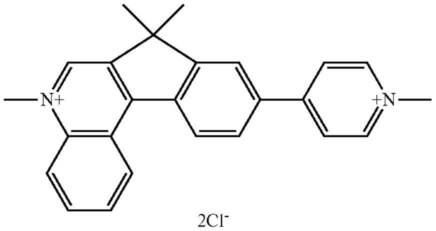

$2Cl^-$

A-2

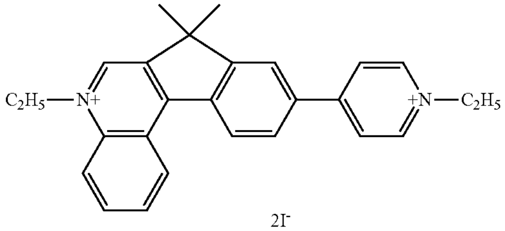

$2I^-$

A-3

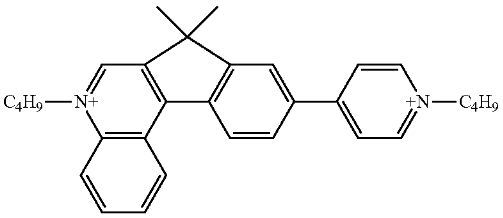

$2(CF_3SO_2)_2N^-$

A-4

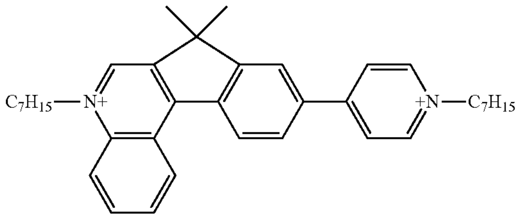

$2(CF_3SO_2)_2N^-$

-continued
A-5
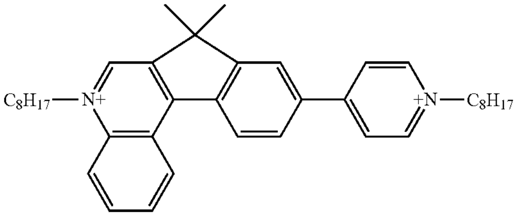
$2CF_3SO_3^-$
A-6
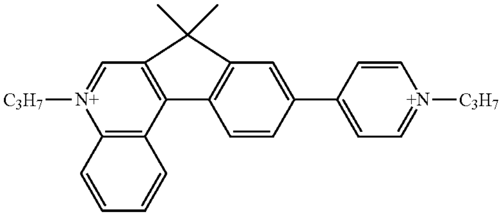
$2ClO_4^-$
A-7
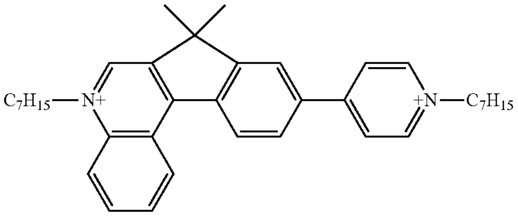
$2Br^-$
A-8
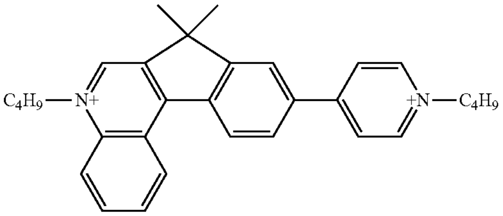
$2BF_4^-$
A-9
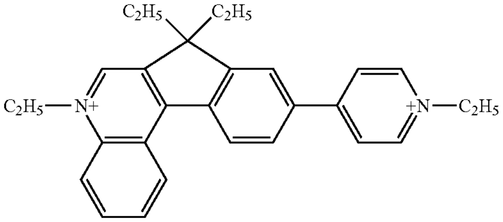
$2I^-$
A-10
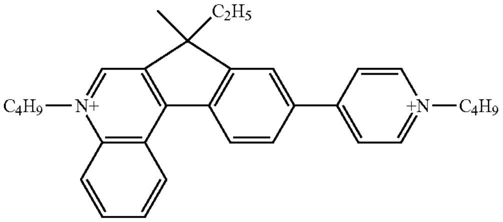
$2(CF_3SO_2)_2N^-$
A-11
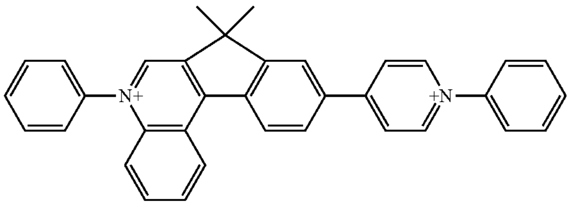
$2Br^-$
A-12
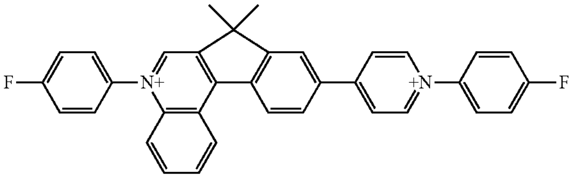
$2PF_6^-$
A-13
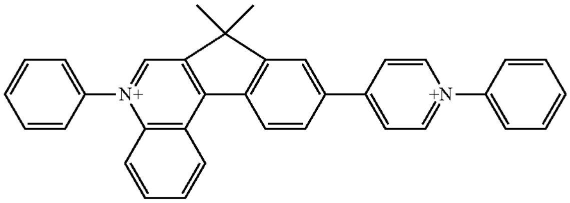
$2PF_6^-$
A-14
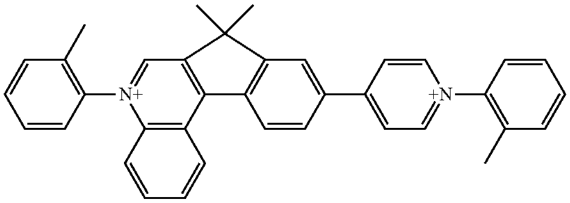
$2(CF_3SO_2)_2N^-$
A-15
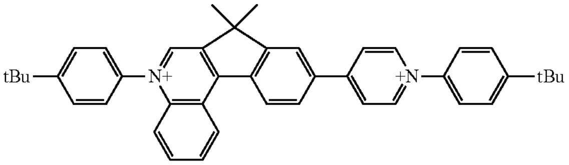
$2Br^-$
A-16
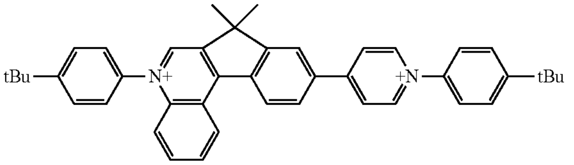
$2(CF_3SO_2)_2N^-$ -continued
A-17
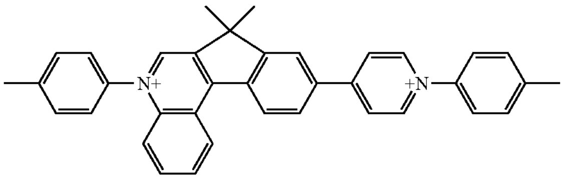
$2Br^-$
A-18
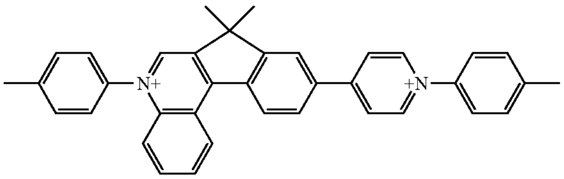
$2(CF_3SO_2)_2N^-$
A-19
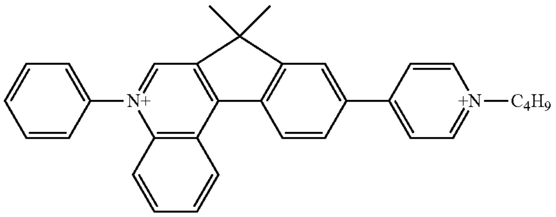
$2(CF_3SO_2)_2N^-$
A-20
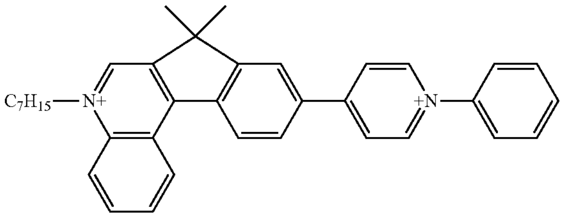
$2PF_6^-$
A-21
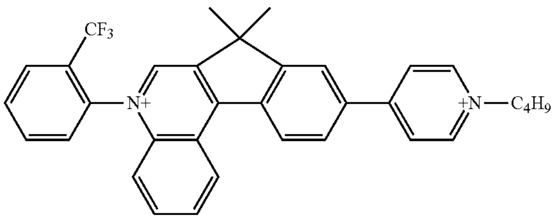
$2BF_4^-$
A-22
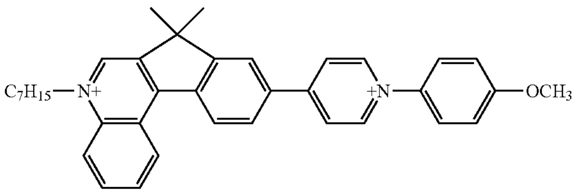
$2PF_6^-$
A-23
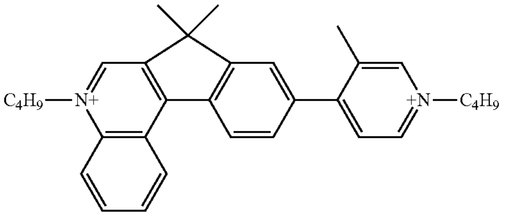
$2PF_6^-$
A-24
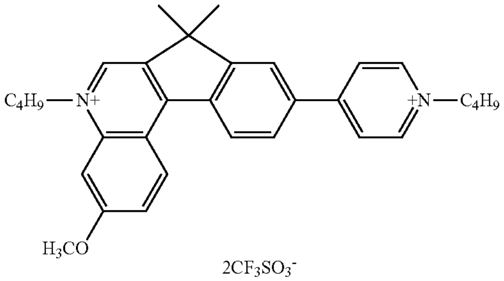
$2CF_3SO_3^-$
A-25
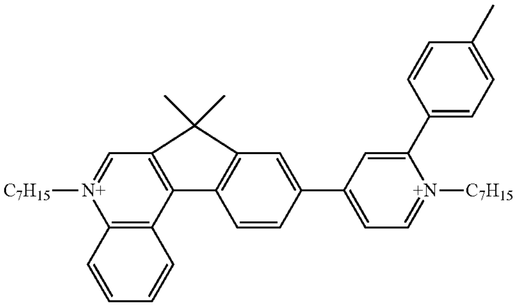
$2CF_3SO_3^-$
A-26
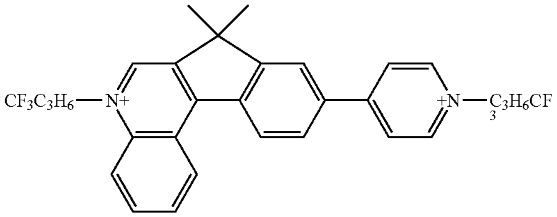
$2CF_3SO_3^-$ -continued
A-27
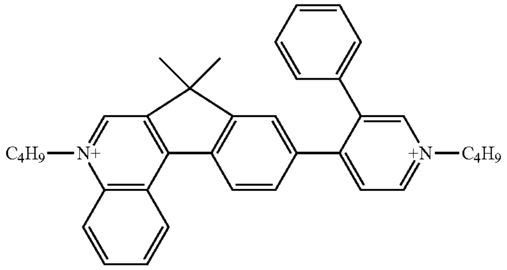
$2PF_6^-$
A-28
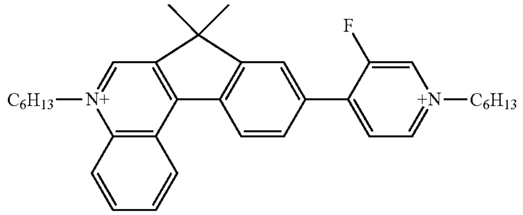
$2PF_6^-$
A-29
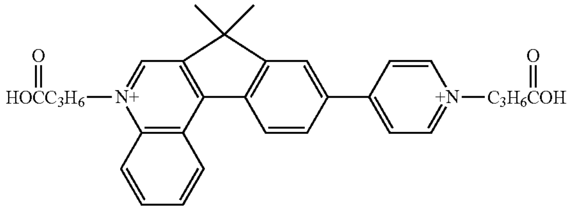
$2(CF_3SO_2)_2N^-$
A-30
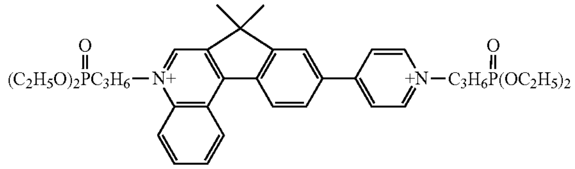
$2PF_6^-$
A-31
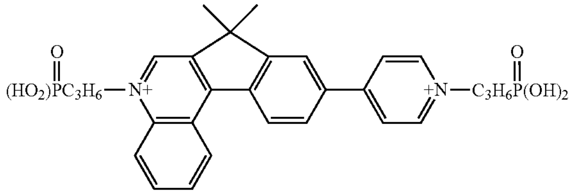
$2PF_6^-$
A-32
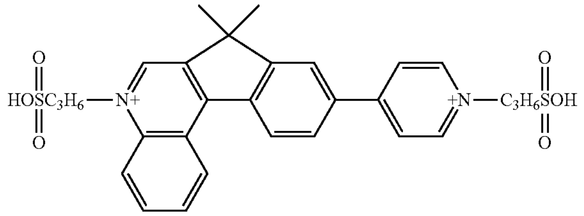
$2PF_6^-$
A-33
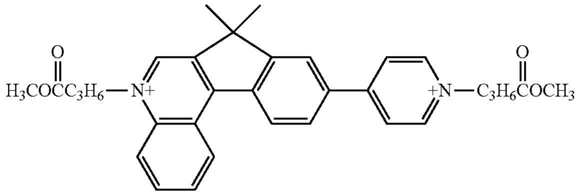
$2PF_6^-$
A-34
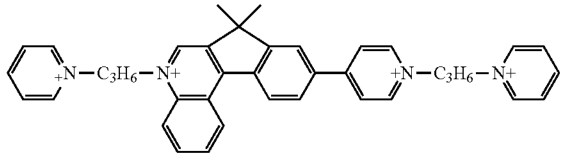
$4PF_6^-$
A-35
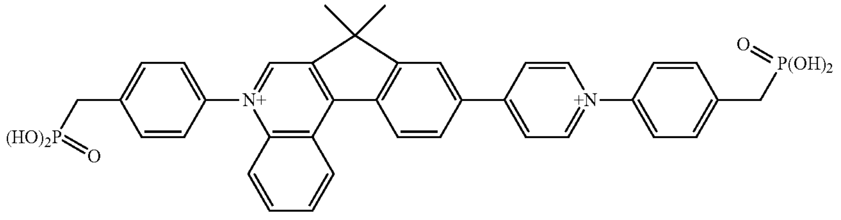
$2CF_3SO_3^-$ -continued

A-36

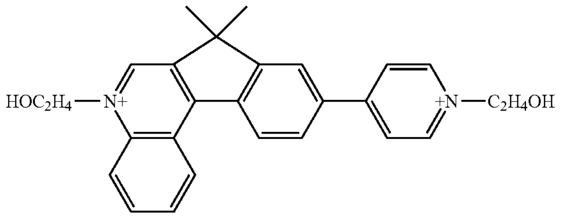

$2(CF_3SO_2)_2N^-$

A-37

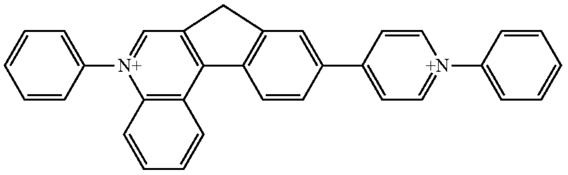

$2(CF_3SO_2)_2N^-$

A-38

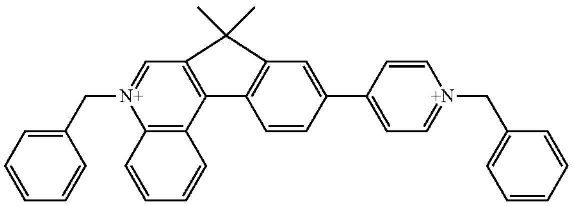

2Br

A-39

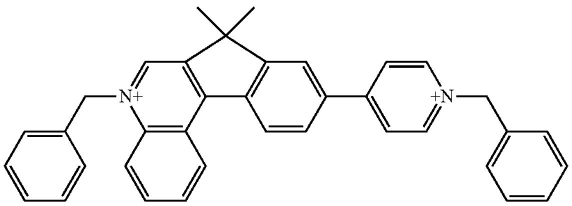

$2PF_6^-$

Among the exemplified compounds above. A-1 to A-10 and A-23 to A-36 are compounds in which $X_1$ and $X_2$ have the same structure. These compounds are easy to synthesize because $X_1$ and $X_2$ have the same structure. Also, these compounds are durable because $X_1$ and $X_2$ are alkyl groups.

Among the exemplified compounds above, A-11 to A-18 and A-37 are compounds in which $X_1$ and $X_2$ have the same structure. These compounds are easy to synthesize because $X_1$ and $X_2$ have the same structure. Also, the absorption wavelength of these compounds is easy to control because $X_1$ and $X_2$ are aryl groups.

Among the exemplified compounds above, A-19 to A-22 are compounds in which $X_1$ and $X_2$ have different structures. Therefore, the absorption wavelength of these compounds is easy to control.

The exemplified compounds above, all of which have the skeleton represented by formula (1), can absorb longer wavelength light.

EC Element

The present organic compound can be used in the EC layer of EC elements. An EC element according to an embodiment will now be described with reference to the drawings.

The EC element 1 depicted in FIG. 1 includes a pair of electrodes 11 and an EC layer 12 disposed between the pair of electrodes. The EC element 1 may further include a pair of transparent substrates 10. The EC element 1 may also include a spacer 13 that keeps the distance between the pair of electrodes 11 constant.

The EC layer 12 contains the organic compound disclosed herein. The EC layer 12 may include a sub-layer made of the present organic compound and a sub-layer containing an electrolyte. Alternatively, the EC layer 12 may be defined by a solution containing an EC compound, namely the present organic compound, and an electrolyte. When the EC layer 12 is defined by a solution, the entirety of the present organic compound, the solution, and other solutes may be referred to as the EC medium.

The components or members of the EC element 1 of the present embodiment will now be described.

Substrates 10

The substrates 10 may be made of, for example, colorless or colored transparent resins, as well as colorless or colored glass or tempered glass. In some embodiments, the substrates 10 are transparent. Transparent substrates used herein refer to those exhibiting a visible light transmittance of 90% or more. Examples of the material of the substrates include polyethylene terephthalate, polyethylene naphthalate, polynorbornene, polyamide, polysulfone, polyether sulfone, polyether ether ketone, polyphenylene sulfide, polycarbonate, polyimide, and polymethyl methacrylate.

Electrodes 11

Exemplary materials of the electrodes 11 include metals and metal oxides, such as indium tin oxide alloy (ITO), fluorine-doped tin oxide (FTO), tin oxide (NESA), indium zinc oxide (IZO), silver oxide, vanadium oxide, molybdenum oxide, gold, silver, platinum, copper, indium, and chromium; silicon-based materials, such as polycrystalline silicon and amorphous silicon; and carbon materials, such as carbon black, graphite, and glassy carbon. In some embodiments, the electrodes 11 are transparent. Transparent electrodes used herein refer to those exhibiting a visible light transmittance of 90% or more.

Conductive polymers whose electric conductivity is increased by doping or the like may also be used as well, and examples include polyaniline, polypyrrole, polythiophene, polyacetylene, poly(para-phenylene), and complexes of polyethylene dioxythiophene (PEDOT) and polystyrene sulfonic acid.

The electrodes 11 may be porous. In some embodiments, the porous electrodes are made of materials with a large surface area, such as microporous materials whose surfaces and internal have micropores, rod-shaped materials, or wire-like materials. For example, the porous electrodes are made of a metal, a metal oxide, or carbon. In some embodiments, the porous electrodes are made of a metal oxide, such as titanium oxide, tin oxide, iron oxide, strontium oxide, tungsten oxide, zinc oxide, tantalum oxide, vanadium oxide, indium oxide, nickel oxide, manganese oxide, or cobalt oxide.

EC Layer 12

Examples of the electrolyte are as follows. When a liquid electrolyte is used, the electrolyte contains an ionically dissociable salt. Any dissociable compound in the solvent can be used as the ionically dissociable salt without limitation. When a solid electrolyte is used, any compound compatible with the present organic compound can be used without limitation. In some embodiments, electron-donating electrolytes may be used. These electrolytes may be referred to as supporting electrolytes. For example, the electrolyte may be an inorganic ionic salt such as an alkali metal salt or an alkaline-earth metal salt, a quaternary ammonium salt, or a cyclic quaternary ammonium salt. Specific examples include Li, Na, and K alkali metal salts, such as $LiClO_4$, LiSCN, $LiBF_4$, $LiAsF_6$, $LiCF_3SO_3$, $LiPF_6$, LiI, NaI, NaSCN, $NaClO_4$, $NaBF_4$, $NaAsF_6$, KSCN, and KCl; and quaternary ammonium salts and cyclic quaternary ammonium salts, such as $(CH_3)_4NBF_4$, $(C_2H_5)_4NBF_4$, $(n\text{-}C_4H_9)_4NBF_4$, $(n\text{-}C_4H_9)_4NPF_6$, $(C_2H_5)_4NBr$, $(C_2H_5)_4NClO_4$, and $(n\text{-}C_4H_9)_4NClO_4$.

The solvent used to dissolve the present organic compound and the electrolyte is not limited provided that it can dissolve these compounds. Examples of the solvent include water and organic solvents, such as methanol, ethanol, propylene carbonate, ethylene carbonate, dimethyl sulfoxide, dimethoxyethane, γ-butyrolactone, γ-valerolactone, sulfolane, dimethylformamide, tetrahydrofuran, acetonitrile, propionitrile, benzonitrile, dimethylacetamide, methylpyrrolidinone, and dioxolane.

The EC layer 12 may further contain polymer or a gelling agent to increase the viscosity or may be gelled.

Such polymer and gelling agents may be referred to as thickeners. Adding a thickener increases the viscosity of the EC solution. High-viscosity EC solutions, in which the movement of molecules is suppressed, hamper the present organic compound from forming associations, reducing the temperature dependence of the absorption spectrum of the organic compound. In some embodiments, therefore, the EC solution contains a thickener.

However, EC solutions with excessively high viscosity do not allow the molecules in the EC solution to move easily, reducing the reaction speed of the EC element. Thus, EC solutions with excessively high viscosity are not suitable.

Specifically, the viscosity of the EC solution may be 10 cP to 5000 cP and, in some embodiments, 50 cP to 1000 cP. The viscosity of the EC solution may be 150 cP or less, for example, 100 cP or less or 65 cP or less. Also, the viscosity of the EC solution may be 20 cP or more, for example, 50 cP or more.

The proportion of the thickener may be 20 wt % or less to 100 wt % of the EC solution. In some embodiments, it may be 1 wt % to 15 wt % or 5 wt % to 10 wt %.

Examples of the polymer include, but are not limited to, polyacrylonitrile, carboxymethyl cellulose, polyvinyl chloride, polyalkylene oxides, polyurethane, polyacrylate, polymethacrylate, polyamide, polyacrylamide, polyester, and Nafion (registered trademark). In some embodiments, polymethyl methacrylate, polyethylene oxide, or polypropylene oxide may be used.

In an embodiment, the EC element may contain one or more other organic compounds (second organic compound) apart from the present organic compound. The second organic compound may be an individual one or includes two or more compounds and may be a compound that colors upon oxidation, a compound that colors upon reduction, or a compound having both characteristics. Organic compounds having the skeleton represented by formula (1) color in the reduced state. Accordingly, second organic compounds desirably color in the oxidized state.

The present organic compound can provide an EC element that can absorb desired colors in combination with the second organic compound. When colors, the second organic compound has an absorption wavelength in the range of 400 nm to 800 nm, for example, 420 nm to 700 nm. Having an absorption wavelength in a specific range means that the absorption spectrum has a peak in the specific range. Combining the present organic compound with two or more second organic compounds can produce an EC element that absorbs light over the entire visible region to color black.

In some embodiments, the EC element contains four or more EC compounds, including the present organic compound. This is because filters including such an EC element tend to absorb light evenly with varying wavelengths.

Examples of the second organic compound are cited below.

Second organic compounds that color upon oxidation include oligothiophene compounds; phenazine-based compounds, such as 5,10-dihydro-5,10-dimethylphenazine and 5,10-dihydro-5,10-di isopropylphenazine; metallocene compounds, such as ferrocene, tetra-t-butylferrocene, and titanocene; phenylenediamine-based compounds, such as N,N',N,N'-tetramethyl-p-phenylenediamine; and pyrazoline compounds, such as 1-phenyl-2-pyrazoline.

Second organic compounds that color upon reduction include viologens, such as N,N'-diheptylbipyridinium diperchlorate, N,N'-diheptylbipyridinium ditetrafluoroborate, N,N'-diheptylbipyridinium dihexafluorophosphate, N,N'-diethylbipyridinium diperchlorate, N,N'-diethylbipyridinium ditetrafluoroborate, N,N'-diethylbipyridinium dihexafluorophosphate, N,N'-dibenzylbipyridinium diperchlorate, N,N'-dibenzylbipyridinium ditetrafluoroborate, N,N'-dibenzylbipyridinium dihexafluorophosphate, N,N'-diphenylbipyridinium diperchlorate, N,N'-diphenylbipyridinium ditetrafluoroborate, and N,N'-diphenylbipyridinium dihexafluorophosphate; anthraquinone compounds, such as 2-ethylanthraquinone, 2-t-butylanthraquinone, and octamethylanthraquinone; ferrocenium salts, such as ferrocenium tetrafluoroborate and ferrocenium hexafluorophosphate; and styryl-based compounds.

Phenazine-based compounds used herein have a chemical structure containing a 5,10-dihydrophenazine skeleton, including compounds containing 5,10-dihydrophenazine with one or more substituents. For example, the hydrogen atoms at the 5- and 10-positions of 5,10-dihydrophenazine may be substituted by alkyl groups with 1 to 8 carbon atoms or aryl groups with 6 to 10 carbon atoms. More specifically, such substituents include alkyl groups, such as methyl, ethyl, propyl, isopropyl, n-butyl, and tert-butyl, and aryl groups, such as phenyl and naphthyl.

The 5,10-dihydrophenazine skeleton may have one or more substituents. Examples of substituents on the 5,10-dihydrophenazine skeleton include alkyl groups with 1 to 20 carbon atoms, aryl groups with 6 to 12 carbon atoms, and aryloxy groups with 6 to 10 carbon atoms. More specifically, such substituents include alkyl groups, such as methyl, ethyl, propyl, n-butyl, and tert-butyl; aryl groups, such as phenyl and naphthyl; and aryloxy groups, such as phenoxy.

The substituent of 5,10-dihydrophenazine skeleton may further have a substituent, such as alkyl groups with 1 to 4 carbon atoms or alkoxy groups with 1 to 4 carbon atoms. Examples of such a substituent include alkyl groups, such as methyl, ethyl, propyl, n-butyl, and tert-butyl; and alkoxy groups, such as methoxy and isopropoxy.

The same applies to substituents of other second organic compounds, such as viologens.

In some embodiments, the second organic compounds are selected from phenazine-based compounds, metallocene compounds, phenylenediamine-based compounds, and pyrazoline-based compounds.

The compounds contained in the EC layer of the EC element disclosed herein can be identified by known extraction and analysis. For example, the compounds may be extracted by chromatography and analyzed by nuclear magnetic resonance (NMR). When the EC layer is solid, the compounds can be analyzed by time-of-flight secondary ion mass spectrometry (TOF-SIMS) or the like.

Spacer 13

The spacer 13 is disposed between the pair of electrodes 11 to define a space that accommodates the EC layer 12. The spacer 13 may be made of polyimide, polytetrafluoroethylene, fluorocarbon rubber, or epoxy resin. The spacer 13 keeps the distance between the electrodes of the EC element 1.

In an embodiment, the EC element may have a liquid inlet defined by the pair of electrodes 11 and the spacer 13. After introducing a composition containing the present organic compound through the liquid inlet, the liquid inlet is covered with a sealing member and further sealed with an adhesive to obtain the EC element 1. The sealing member also serves to isolate the composition from the adhesive so as not to come into contact with each other. The sealing member may have any shape without limitation but is, in some embodiments, tapered like wedges or the like.

The EC element disclosed herein may be produced by any method without limitation and, for example, by introducing a liquid containing EC compounds prepared in advance into the space between the pair of electrodes 11, using vacuum injection, atmospheric injection, meniscus, or the like.

Applications of EC Element

When operating, the EC element disclosed herein can adjust the amount of light passing through the EC layer. The EC element can be used in optical filters, lens units, imaging devices, windows, and the like.

Optical Filter

An optical filter according to an embodiment of the present disclosure includes an EC element 1 and an active element connected to the EC element 1. The optical filter may include peripheral devices. The active element may be connected to the EC element 1 directly or indirectly with another element therebetween. The active element drives the EC element 1 and adjusts the amount of light passing through the EC element. The active element may be a transistor. The transistor may contain a semiconductor material, such as InGaZnO, in the active region.

Figure 2:
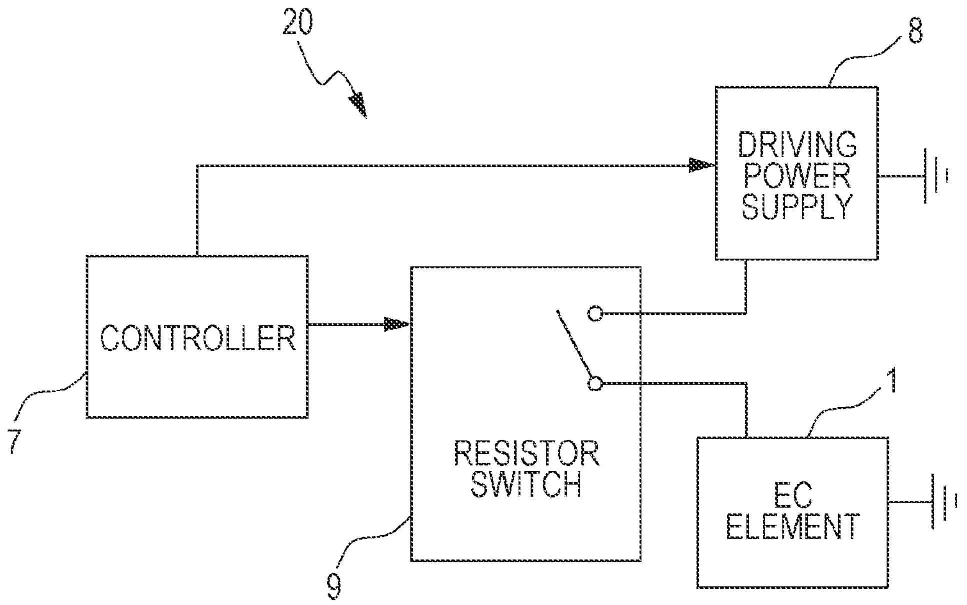
FIG. 2 is a schematic diagram of a drive unit including an electrochromic element according to an embodiment.

The optical filter in the present embodiment includes the EC element disclosed herein and a drive unit connected to the EC element. FIG. 2 is a schematic diagram of a drive unit 20 and the EC element 1 driven by the drive unit 20. In the illustrated embodiment, the drive unit 20 further includes a controller 7, a driving power supply 8, and a resistor switch 9.

The driving power supply 8 applies a voltage required for the electrochemical reaction of the EC compounds in the EC layer 12 (hereinafter also referred to as "driving voltage") to the EC element 1. In some embodiments, the driving voltage is constant. This is because when the EC layer 12 contains a plurality of EC compounds, the absorption spectrum may change due to the differences in redox potential and molar absorption coefficient among the EC compounds. Driving voltage application is started and kept by signals from the controller 7. In an embodiment, the application of a constant voltage is maintained while the optical transmittance of the EC element 1 is controlled.

The controller 7 controls the transmittance of the EC element 1 suitably for the EC element 1. More specifically, conditions previously required for a desired transmittance may be input to the EC element 1, or conditions to meet the set value of the transmittance may be selected according to the comparison between the set transmittance and the transmittance of the EC element 1. Parameters to be varied include voltage, current, and duty cycle. The term duty cycle used herein refers to the proportion of one period of the applied voltage duration within the period of a pulse voltage waveform. The controller 7 can vary the voltage, current, or duty cycle to change the color density of the EC element 1.

In the embodiments disclosed herein, known techniques can be used for varying voltage and current and modulating the pulse width. Also, the pulse width may be modulated as described below.

The resistor switch 9 switches between resistor $R_1$ and resistor $R_2$ with higher resistance than $R_1$ (both resistors not shown) and connects either resistor in series in a closed circuit including drive power supply 8 and EC element 1. The resistance of resistor $R_1$ may be lower than at least the highest impedance in the closed circuit of the element and is, in some embodiments, 10Ω or less. The resistance of resistor $R_2$ may be higher than the highest impedance in the closed circuit of the element and is, in some embodiments, 1 MΩ or more. Resistor $R_2$ may be air. In this instance, the closed circuit is open in strict meaning but can be considered closed, provided that air is interpreted as resistor $R_2$.

The controller 7 sends signals to the resistor switch 9 to control the switching between resistors $R_1$ and $R_2$. When resistor $R_1$ is on, the EC element 1 colors, and when resistor $R_2$ is on, the EC element 1 achromatizes. While resistor $R_2$ is on, EC compounds self-achromatize. This self-achromatizing is caused, for example, by instability of radicals of EC compounds produced in coloring, diffusion of the radicals to the opposing electrode with a different potential, or collision between anodic radicals and cathodic radicals in the solution.

Lens Unit

The lens unit disclosed herein according to an embodiment of the disclosure includes an imaging optical system, and an optical filter including the EC element disclosed herein. The imaging optical system may include one or more lenses. The optical filter may be disposed between or among the lenses or outside the lenses. In some embodiments, the optical filter is disposed on the optical axis of the lenses.

Imaging Device

The imaging device in an embodiment includes an optical filter including the EC element disclosed herein, and a light-receiving element configured to receive light passing through the optical filter. Specific examples of the imaging device include cameras, video cameras, and camera phones. The imaging device may be such that a lens unit including one or more lenses is separable from the main body including the light-receiving element. In an embodiment in which the lens unit is separable from the main body of the imaging device, an optical filter, apart from the imaging device, may be used for imaging. At this time, the optical filter may be placed outside the lens unit, between the lens unit and the light-receiving element, or between or among the lenses (when the lens unit includes a plurality of lenses).

Figure 3A:
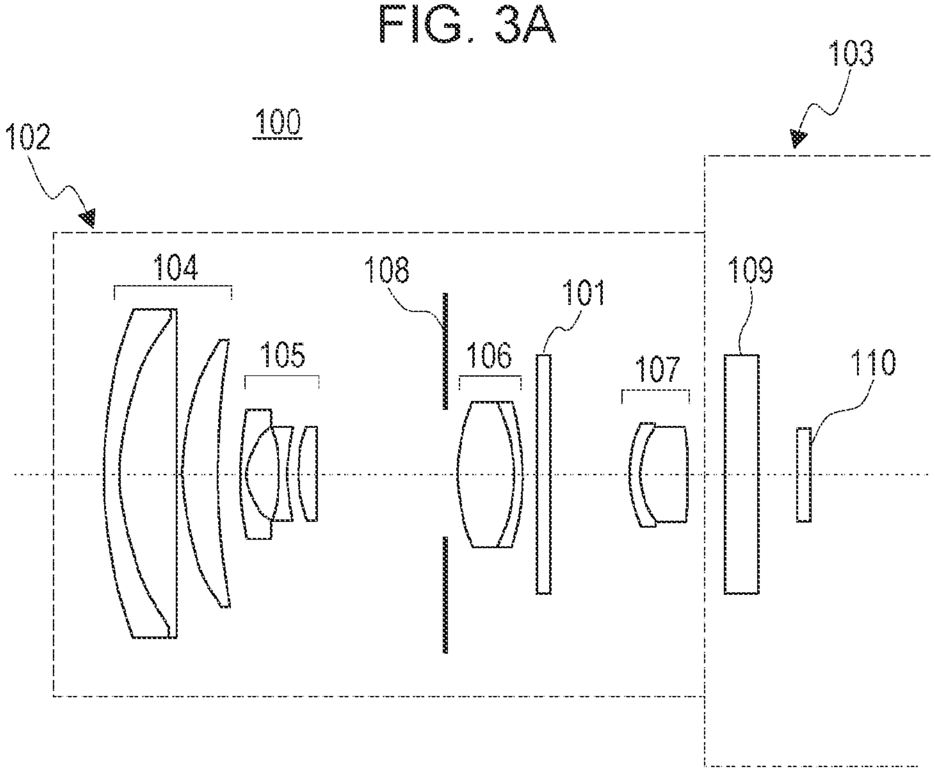
FIG. 3A is a schematic diagram of an imaging device in which an optical filter is disposed in the lens unit.

FIG. 3A is a schematic diagram of an imaging device in which an optical filter is disposed in the lens unit, and FIG.

3B is a schematic diagram of an imaging device in which an optical filter is disposed in the main body (imaging unit) of the imaging device.

The imaging device 100 includes a lens unit 102 and an imaging unit 103. The lens unit 102 includes an optical filter 101 and an imaging optical system including lenses. The optical filter 101 is the optical filter disclosed herein described above. The number of lenses may be single or plural.

For example, the lens unit 102 may act as a rear focusing zoom lens that focuses behind the diaphragm. The lens unit 102 includes four lens sets arranged in the following order from the imaging subject (object): a first lens set 104 having a positive refractive power, a second lens set 105 having a negative refractive power, a third lens set 106 having a positive refractive power, and a fourth lens set 107 having positive refractive power. The imaging device may focus, for example, by varying the distance between the second lens set 105 and the third lens set 106 to vary magnification and moving some lenses of the fourth lens set 107.

For example, the lens unit 102 may include an aperture diaphragm 108 between the second lens set 105 and the third lens set 106 and the optical filter 101 between the third lens set 106 and the fourth lens set 107. The lens unit 102 is configured to allow light to pass through the lens sets 104 to 107, the diaphragm 108, and the optical filter 101 to adjust the amount of light with the aperture diaphragm 108 and the optical filter 101.

The lens unit 102 may be removably connected to the imaging unit 103 with a mounting member (not shown).

Although in the present embodiment, the optical filter 101 is disposed between the third lens set 106 and the fourth lens set 107 in the lens unit 102, the imaging device 100 is not limited by this configuration. For example, the optical filter 101 may be disposed in front of the aperture diaphragm 108 (on the imaging subject side), behind the aperture diaphragm (on the imaging unit 103 side), in front of or behind any of the first to fourth lens sets 104 to 107, or between any two of the lens sets. Placing the optical filter 101 at the position where light converges advantageously reduces the area of the optical filter 101.

The configuration of the lens unit 102 may also be selected as desired without being limited to that described above.

The lens unit may be of a type other than the rear focusing type and may be, for example, of an inner focusing type that focuses on a position in front of the diaphragm. Also, the lens unit may act as a special lens, such as a fisheye lens or a microlens, as well as the zoom lens.

The imaging unit 103 includes a glass block 109 and a light-receiving element 110. The glass block 109 may be a low-pass filter, a face plate, or a color filter. The light-receiving element 110 is a sensor that receives light passing through the lens unit, and an imaging element, such as CCD or CMOS, may be used. Alternatively, the light-receiving element may be a light sensor such as a photodiode or any other element or device capable of obtaining and outputting information such as light intensity or wavelength.

When the optical filter 101 is incorporated in the lens unit 102, as depicted in FIG. 3A, the drive unit 20 may be placed within or outside the lens unit 102. In the case of placing the lens unit 102 outside, the drive unit 20 is connected for drive control to the EC element 1 of the lens unit 102 with a wire.

In the above-described imaging device 100, the optical filter 101 is located inside the lens unit 102. However, the configuration is not limited to this, provided that the optical filter 101 is located at a position inside the imaging device 100 so that the light-receiving element 110 can receive the light passing through the optical filter 101.

Figure 3B:
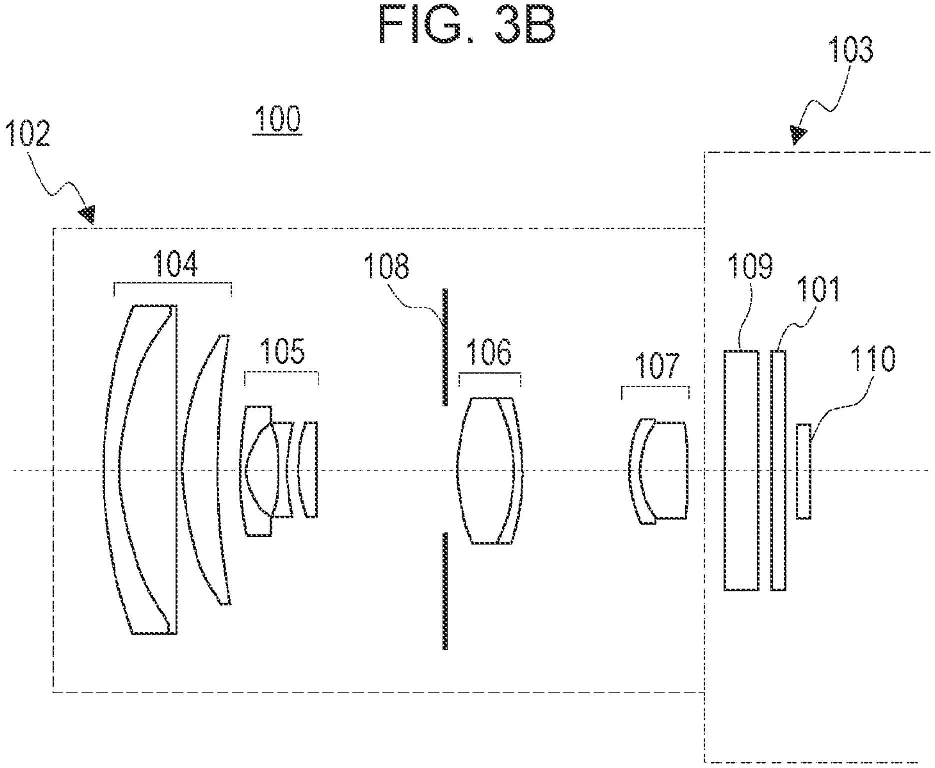
FIG. 3B is a schematic diagram of an imaging device in which an optical filter is disposed in the main body of the imaging device.

For example, the imaging unit 103 may have the optical filter 101, as depicted in FIG. 3B. FIG. 3B is a schematic diagram of another embodiment of the imaging device disclosed herein, illustrating a configuration in which the optical filter is located in the imaging unit 103. In FIG. 3B, the optical filter 101 is located, for example, right in front of the light-receiving element 110. In a configuration in which the imaging device itself incorporates an optical filter 101, the lens unit 102 to be connected need not include the optical filter 101. Accordingly, a dimmable imaging device can be configured using an existing lens unit 102.

The imaging device 100 disclosed herein can be applied to products including a combination of a light-receiving element and the function of adjusting the amount of light. For example, the imaging device may be a camera, a digital camera, a video camera, or a digital video camera and can also be used in products, such as mobile phones, smartphones, PCs, and tablet computers, which incorporate an imaging device.

In the imaging device 100 disclosed herein, an optical filter 101 can be used as a dimmer member to enable a single filter to vary the dimming level as appropriate. This is advantageous for reducing the number of components and saving space.

Window

A window according to an embodiment of the disclosure includes a pair of substrates, the EC element disclosed herein disposed between the pair of substrates, and an active element connected to the EC element. The window adjusts the amount of light passing through the EC element 1 with the active element connected as a driver to the EC element 1 for driving the EC element 1 but is not limited to this. The active element may be a transistor. The transistor may contain a semiconductor material, such as InGaZnO, in the active region. The window disclosed herein may be called a variable transmittance window.

Figure 4A:
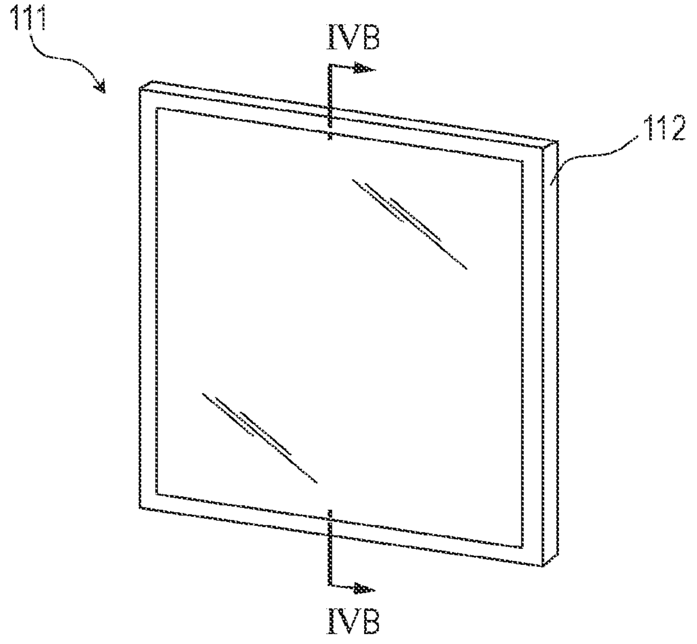
FIG. 4A is an external view of a window using an EC element according to an embodiment.
Figure 4B:
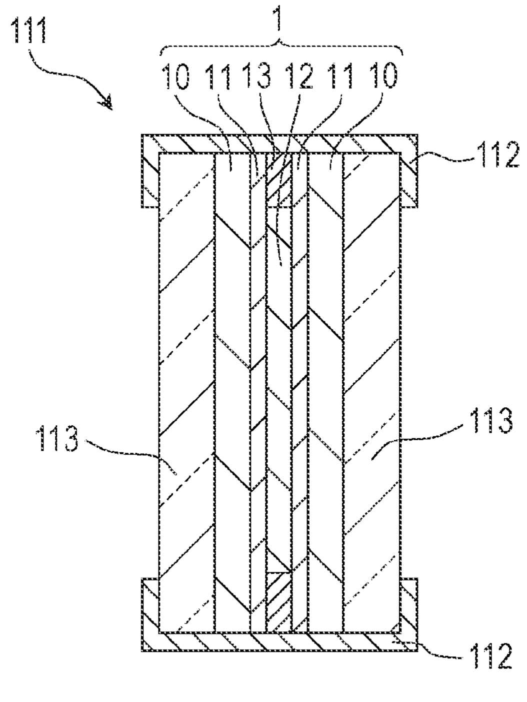
FIG. 4B is a schematic sectional view taken along line IVB-IVB in FIG. 4A.

FIG. 4A is an external view of a dimming window 111 used as a window using the EC element disclosed herein, and FIG. 4B is a schematic sectional view taken along line IVB-IVB in FIG. 4A. The dimming window disclosed herein includes an EC element 1 (optical filter) and transparent plates 113 holding the EC element in between, and a frame 112. The EC element 1 is provided with a drive unit (not shown). The drive unit may be integrated with the frame 112 or located outside the frame 112 and connected to the EC element 1 with a wire.

The frame 112 may be made of any material without limitation, and a structure in that covers at least a portion of the EC element 1 and has an integrated form may be considered the frame. While the EC element 1 depicted in FIG. 4B is a component member apart from the transparent plates 113, the substrates 10 of the EC element 1 may be considered transparent plates 113, for example.

The material of the transparent plates 113 is not limited, provided that the material has high light transmittance. In some embodiments, glass is used in view of use as a window.

The dimming window disclosed herein may be used, for example, to adjust the amount of sunlight entering a room during the daytime. The dimming window may also be used to adjust the amount of heat as well as the amount of sunlight, controlling the brightness and temperature in a room. Additionally, the dimming window may be used as a shutter to block views from the outside to the interior. In addition to windows for buildings, such a dimming window may be used as a window for vehicles such as cars, trains, airplanes, and ships.

The EC element may be provided with a reflection member in one of the light paths. Such a window is called an EC mirror. The EC mirror includes a pair of substrates, the EC element disclosed herein between the pair of substrates, an active element connected to the EC element, and the reflection member. The EC mirror may be provided as an anti-glare mirror in a car or the like.

Thus, the EC element 1 including the EC layer 12 containing the organic compound having the skeleton represented by formula (1) or the organic compound represented by formula (2) can be used in optical filters, lens units, imaging devices, and windows. In the optical filter, lens unit, imaging device, and window according to the present disclosure, the organic compound represented by formula (1) or (2) may be used alone or combined with other EC compounds that absorb colors with other wavelengths. Thus, various colors can be absorbed.

Also, the disclosed optical filter, lens unit, imaging device, and window each contain the organic compound represented by formula (1) or (2), thereby exhibiting increased transparency in the achromatizing state.

EXAMPLES

The concept of the disclosure will be further described in detail with reference to the Examples below. However, the implementation of the disclosure is not limited to the Examples disclosed below.

Example 1

Synthesis of Exemplified Compound A-11

(1) Synthesis of Intermediate 11

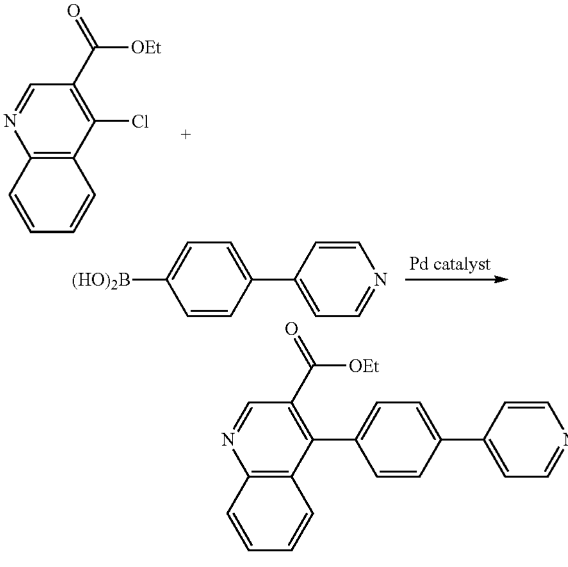

Intermediate 11

A reaction vessel was charged with ethyl 4-chloroquinoline-3-carboxylate (646 mg, 2.7 mmol), 4-(4'-pyridyl)phenylboronic acid (600 mg, 3.0 mmol), 1,4-dioxane (15 mL), and water (5 mL), and dissolved oxygen was removed with nitrogen. Then, tetrakis(triphenylphosphine)palladium(0) (62 mg, 0.053 mmol) and tripotassium phosphate (1.5 g, 7.1 mmol) were added in a nitrogen atmosphere, followed by a reaction at 100° C. for 8 hours. After cooling the reaction solution, water and ethyl acetate were added, and the oil phase was extracted. The oil phase was subjected to separation and purification by silica gel chromatography (mobile phase: hexane/ethyl acetate) to yield Intermediate 11 (584 mg, 61% yield).

(2) Synthesis of Intermediate 12

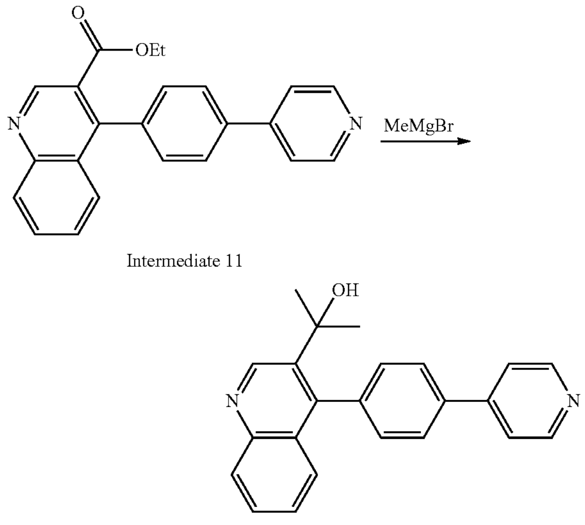

Intermediate 11

Intermediate 12

A reaction vessel was charged with Intermediate 11 (532 mg, 1.5 mmol) and anhydrous tetrahydrofuran (20 mL) and cooled to −5° C. Then, methylmagnesium bromide solution (about 3.0 M in Tetrahydrofuran, 4 mL, 12.0 mmol) was slowly dropped. After being stirred for 1 hour, the solution was warmed to room temperature. An ammonium chloride solution was added to the solution to stop the reaction, followed by extraction with methyl acetate. The extract was subjected to separation and purification by silica gel chromatography (mobile phase: chloroform/methanol) to yield Intermediate 12 (424 mg, 83% yield).

(3) Synthesis of Intermediate 13

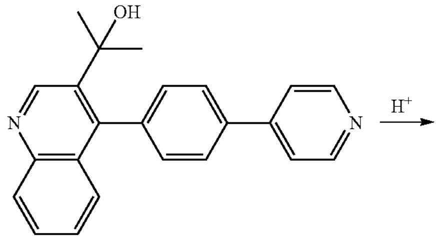

Intermediate 12

-continued

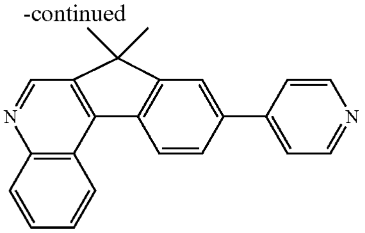

Intermediate 13

A reaction vessel was charged with Intermediate 12 (424 mg, 1.2 mmol) and trifluoromethanesulfonic acid (5 mL), followed by stirring at 80° C. for 8 hours. The solution was neutralized with a sodium hydroxide aqueous solution, followed by extraction with ethyl acetate. The extract was subjected to separation and purified by silica gel chromatography (mobile phase: hexane/ethyl acetate) to yield Intermediate 13 (361 mg, 90% yield).

(4) Synthesis of Exemplified Compound A-11

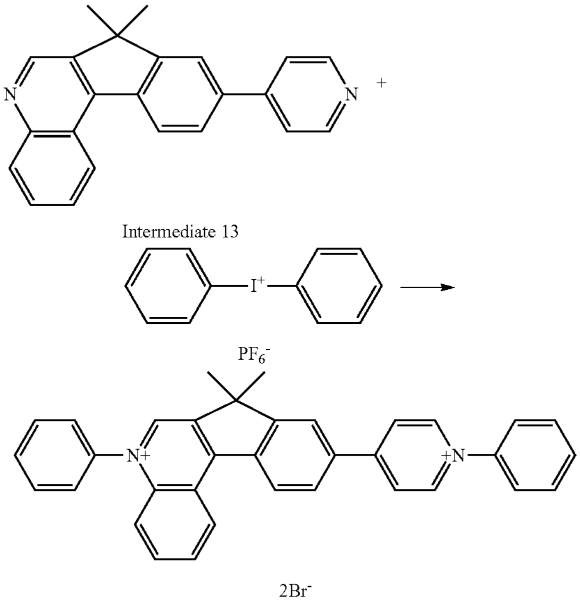

A-11

A reaction vessel was charged with Intermediate 13 (161 mg, 0.5 mmol), diphenyliodonium hexafluorophosphate (2.13 g, 5 mmol), copper (II) acetate monohydrate (18 mg, 0.10 mmol), and N,N-dimethylformamide (2.5 mL), followed by a reaction at 100° C. for 40 hours. After completion of the reaction, the reaction solution was concentrated under reduced pressure, and a solution (10 mL) of tetrabutylammonium bromide (2 g) in acetonitrile was added. Precipitated solids were collected by filtration to yield Exemplified Compound A-11 (0.21 g, 66% yield).

The structure of Exemplified Compound A-11 was identified by $^1$H NMR analysis.

$^1$H NMR ($CD_3CN$, 500 MHz) δ (ppm): 9.85 (s, 1H), 9.40 (d, 1H), 9.36 (d, 2H), 9.15 (d, 1H), 8.82 (d, 2H), 8.68 (s, 1H), 8.47 (d, 1H), 8.20 (m, 2H), 7.94-7.75 (m, 11H), 1.89 (s, 6H)

Example 2

Synthesis of Exemplified Compound A-13

Exemplified Compound A-11 (0.13 g, 0.2 mmol) was dissolved in water, and an aqueous solution in which 200 mg of ammonium hexafluorophosphate was dissolved was dropped, followed by stirring at room temperature for 3 hours. Precipitated crystals were collected by filtration and rinsed with water, isopropyl alcohol, and diethyl ether in this order to yield Exemplified Compound A-13 (143 mg, 93% yield).

The structure of Exemplified Compound A-13 was identified by $^1$H NMR analysis.

$^1$H NMR ($CD_3CN$, 500 MHZ) δ (ppm): 9.35 (s, 1H), 9.25 (d, 1H), 9.06 (d, 2H), 8.99 (d, 1H), 8.64 (d, 2H), 8.48 (s, 1H), 8.34 (d, 1H), 8.15 (m, 2H), 7.88-7.71 (m, 11H), 1.82 (s, 6H)

Example 3

Fabrication and Property Evaluation of EC Element

An electrolyte, tetrabutylammonium perchlorate, was dissolved to 0.1 M in propylene carbonate, and Exemplified Compound A-13 in Example 2 was subsequently dissolved to 40.0 mM to yield an EC solution.

Then, a pair of glass substrates with a transparent conductive film (ITO) were each provided with an insulating layer (SiO2) on the four ends. A PET film (Melinex (registered trademark) S manufactured by Dupont Teijin Films, 125 μm thick) was disposed between the pair of transparent conductive film-provided glass substrates to define a gap between the substrates. Then, the substrates and the PET film were bonded with an epoxy adhesive for sealing, leaving an inlet through which the EC medium would be introduced. Thus, a hollow cell with an inlet was fabricated.

Then, the EC solution prepared above was introduced into the cell through the inlet by vacuum injection, and the inlet was sealed with the epoxy adhesive to obtain an EC element.

The EC element immediately after production Immediately after fabrication exhibited a transmittance of about 80% over the entire visible region and was thus highly transparent.

Figure 5:
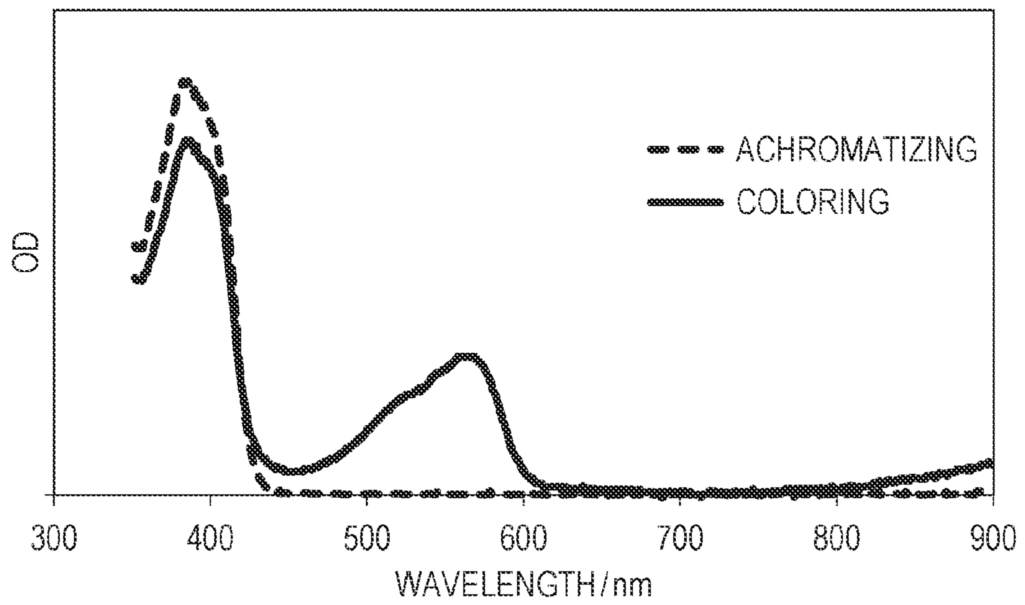
FIG. 5 is a plot of UV-visible absorption spectra of Example Compound A-13 in a coloring state and an achromatizing state.

When a voltage of 2.0 V was applied, the EC element exhibited an absorption (λmax=570 nm) derived from a reduced form of Exemplified Compound A-13 and colored. When-0.5 V was applied, the EC element achromatized. This element can change reversibly between a coloring state and an achromatizing state. FIG. 5 illustrates UV-visible absorption spectra of the element fabricated in Example 3. The light source was a DH-2000S light source using deuterium and halogen lamps manufactured by Ocean Optics, Inc.

Example 4

Synthesis of Exemplified Compound A-7

A reaction vessel was charged with Intermediate 13 (161 mg, 0.5 mmol), 1-bromoheptane (448 mg, 2.5 mmol), and N,N-dimethylformamide (5 mL), followed by a reaction at 100° C. for 48 hours. After completion of the reaction, precipitated solids were collected by filtration and rinsed with acetonitrile to yield 0.28 g of Exemplified Compound A-7 (82% yield).

The structure of Exemplified Compound A-7 was identified by $^1$H NMR analysis.

$^1$H NMR (DMSO-d6, 500 MHz) δ (ppm): 9.99 (s, 1H), 9.34 (d, 1H), 9.24 (d, 2H), 9.06 (d, 1H), 8.77 (d, 2H), 8.71

(m, 2H), 8.35 (m, 2H), 8.18 (t, 1H), 5.09 (t, 1H), 4.65 (t, 1H), 2.01 (m, 4H), 1.78 (s, 6H), 1.48-1.21 (m, 16H), 0.87 (m, 6H)

Example 5

Synthesis of Exemplified Compound A-4

Exemplified Compound A-7 (136 mg, 0.2 mmol) was dissolved in water. An aqueous solution in which lithium bis(trifluoromethanesulfonyl)imide (0.29 g, 1 mmol) was dissolved was dropped, followed by stirring at room temperature for 3 hours. Precipitated crystals were collected by filtration and rinsed with isopropyl alcohol and diethyl ether in this order to yield 195 mg of Exemplified Compound A-4 (90% yield).

The structure of Exemplified Compound A-4 was identified by $^1$H NMR analysis.

$^1$H NMR (DMSO-d6, 500 MHz) δ (ppm): 9.99 (s, 1H), 9.34 (d, 1H), 9.24 (d, 2H), 9.06 (d, 1H), 8.77 (d, 2H), 8.71 (m, 2H), 8.35 (m, 2H), 8.18 (t, 1H), 5.09 (t, 1H), 4.65 (t, 1H), 2.01 (m, 4H), 1.78 (s, 6H), 1.48-1.21 (m, 16H), 0.87 (m, 6H)

Example 6

Fabrication and Property Evaluation of EC Element

Figure 6:
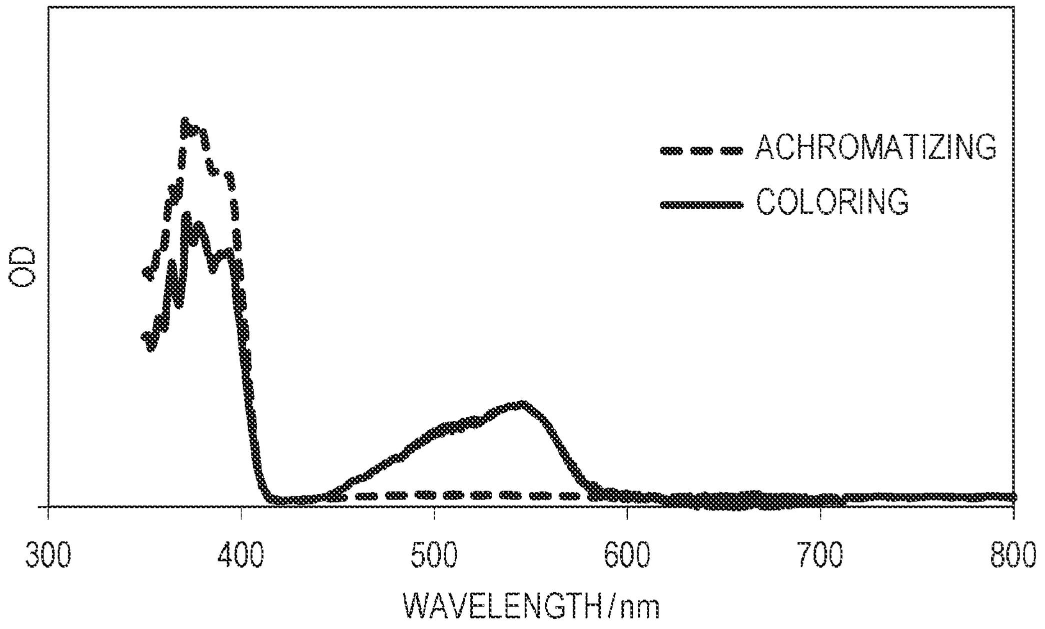
FIG. 6 is a plot of UV-visible absorption spectra of Example Compound A-4 in a coloring state and an achromatizing state.

An element was fabricated in the same manner as Example 3, except for using Exemplified Compound A-4 instead of Exemplified compound A-13, which was used in Example 3. When a voltage of 2.2 V was applied, the element exhibited an absorption (λmax=541 nm) derived from a reduced form of Exemplified Compound A-4. When-0.5 V was applied, the element achromatized, thus reversibly coloring and achromatizing. FIG. 6 illustrates UV-visible absorption spectra of the element fabricated in Example 6.

Example 7

Synthesis of Exemplified Compound A-15

A reaction vessel was charged with Intermediate 13 (161 mg, 0.5 mmol), di-tert-butylphenyliodonium hexafluorophosphate (2.69 g, 5 mmol), copper (II) acetate monohydrate (18 mg, 0.10 mmol), and N,N-dimethylformamide (2.5 mL), followed by a reaction at 100° C. for 48 hours. After completion of the reaction, the reaction solution was concentrated under reduced pressure, and a solution (10 mL) of tetrabutylammonium bromide (2 g) in acetonitrile was added. Precipitated solids were collected by filtration to yield Exemplified Compound A-15 (0.22 g, 60% yield).

The structure of Exemplified Compound A-15 was identified by $^1$H NMR analysis.

$^1$H NMR (DMSO-d6, 500 MHz) δ (ppm): 10.01 (s, 1H), 9.51 (d, 2H), 9.44 (d, 1H), 9.18 (d, 1H), 8.95 (d, 2H), 8.88 (s, 1H), 8.53 (d, 1H), 8.21 (m, 2H), 7.91-7.73 (m, 9H), 1.80 (s, 6H), 1.44 (s, 9H), 1.40 (s, 9H)

Example 8

Synthesis of Exemplified Compound A-16

Exemplified Compound A-15 (0.15 g, 0.2 mmol) was dissolved in water, and an aqueous solution in which 0.3 g of lithium bis(trifluoromethanesulfonyl)imide was dissolved was dropped, followed by stirring at room temperature for 3 hours. Precipitated crystals were collected by filtration and rinsed with water, isopropyl alcohol, and diethyl ether in this order to yield Exemplified Compound A-15 (218 mg, 95% yield).

The structure of Exemplified Compound A-16 was identified by $^1$H NMR analysis.

$^1$H NMR ($CD_3CN$, 500 MHz) δ (ppm): 9.35 (s, 1H), 9.25 (d, 1H), 9.06 (d, 2H), 8.99 (d, 1H), 8.64 (d, 2H), 8.48 (s, 1H), 8.34 (d, 1H), 8.15 (m, 2H), 7.88-7.71 (m, 11H), 1.82 (s, 6H)

Example 9

Fabrication and Property Evaluation of EC Element

Figure 7:
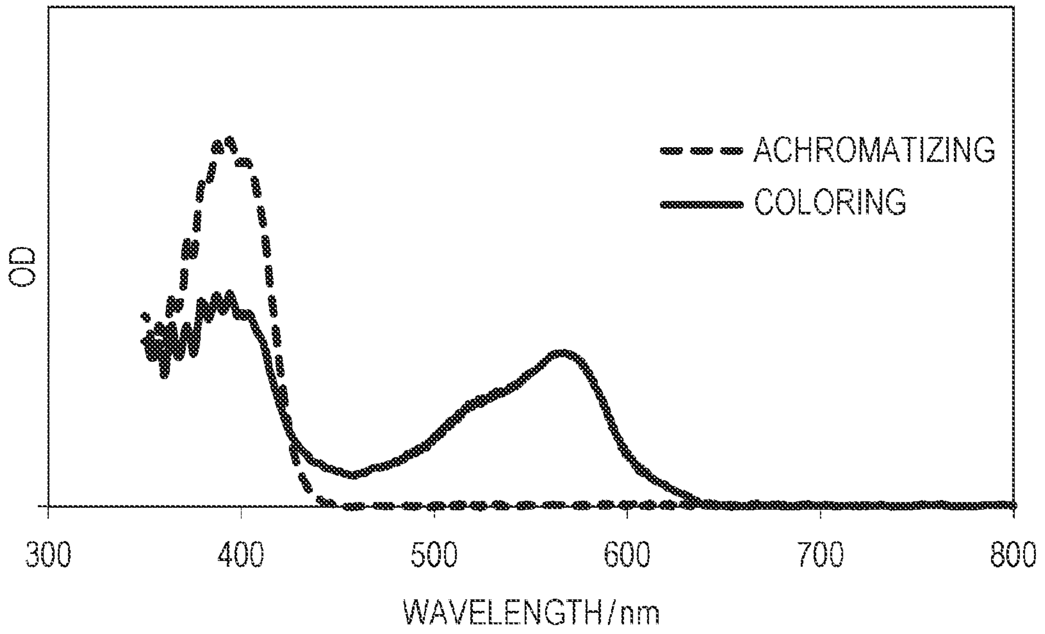
FIG. 7 is a plot of UV-visible absorption spectra of Example Compound A-16 in a coloring state and an achromatizing state.

An element was fabricated in the same manner as Example 3, except for using Exemplified Compound A-16 instead of Exemplified compound A-13, which was used in Example 3. When a voltage of 2.2 V was applied, the element exhibited an absorption (λmax=567 nm) derived from a reduced form of Exemplified Compound A-16. When-0.5 V was applied, the element achromatized, thus reversibly coloring and achromatizing. FIG. 7 illustrates UV-visible absorption spectra of the element fabricated in Example 9.

Example 10

Synthesis of Exemplified Compound A-38

A reaction vessel was charged with Intermediate 13 (161 mg, 0.5 mmol), benzyl bromide (342 mg, 2.0 mmol), and acetonitrile (10 mL), followed by a reaction at 80° C. for 8 hours. After completion of the reaction, precipitated solids were collected by filtration to yield 0.32 g of Exemplified Compound A-38 (95% yield).

The structure of Exemplified Compound A-38 was identified by $^1$H NMR analysis.

$^1$H NMR (DMSO-d6, 500 MHz) δ (ppm): 10.28 (s, 1H), 9.36 (m, 3H), 9.09 (d, 1H), 8.80 (d, 1H), 8.71 (s, 1H) 8.56 (d, 1H), 8.36 (d, 1H), 8.24 (t, 1H), 8.13 (t, 1H), 7.60 (d, 2H), 7.52-7.43 (m, 3H), 7.42-7.33 (m, 5H), 6.40 (s, 2H), 5.92 (s, 2H), 1.81 (s, 6H)

Example 11

Synthesis of Exemplified Compound A-39

Exemplified Compound A-38 (0.13 g, 0.2 mmol) was dissolved in water, and an aqueous solution in which 200 mg of ammonium hexafluorophosphate was dissolved was dropped, followed by stirring at room temperature for 3 hours. Precipitated crystals were collected by filtration and rinsed with water, isopropyl alcohol, and diethyl ether in this order to yield Exemplified Compound A-39 (140 mg, 88% yield).

The structure of Exemplified Compound A-39 was identified by $^1$H NMR analysis.

$^1$H NMR ($CD_3CN$, 500 MHz) δ (ppm): 9.35 (s, 1H), 9.25 (d, 1H), 9.06 (d, 2H), 8.99 (d, 1H), 8.64 (d, 2H), 8.48 (s, 1H), 8.34 (d, 1H), 8.15 (m, 2H), 7.88-7.71 (m, 11H), 1.82 (s, 6H)

Example 12

Fabrication and Property Evaluation of EC Element

Figure 8:
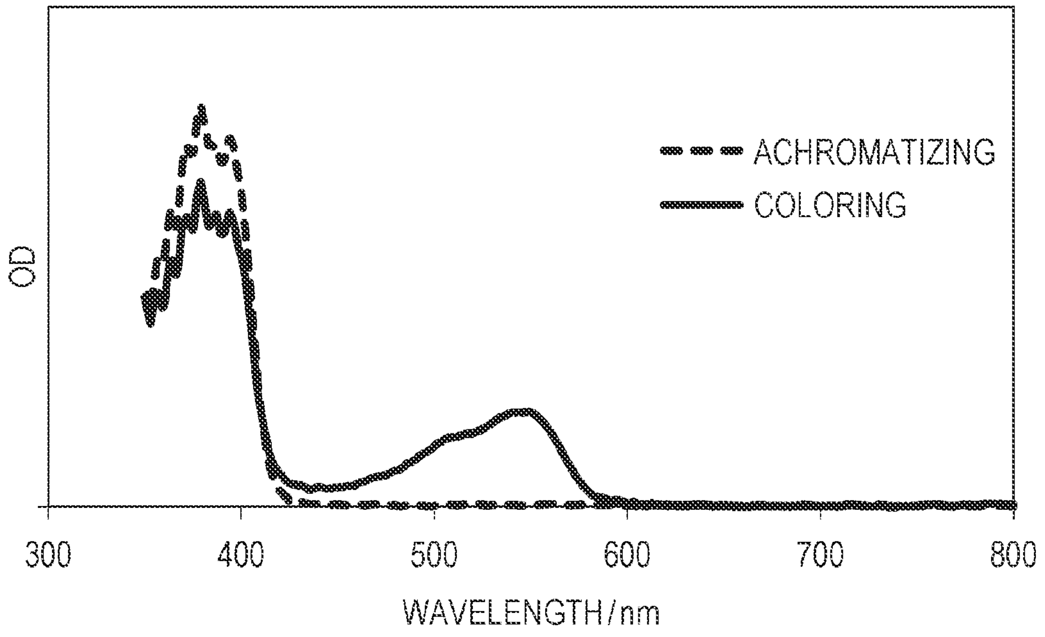
FIG. 8 is a plot of UV-visible absorption spectra of Exemplified Compound A-39 in a coloring state and an achromatizing state.

An element was fabricated in the same manner as Example 3, except for using Exemplified Compound A-39 instead of Exemplified compound A-13, which was used in Example 3. When a voltage of 2.2 V was applied, the element exhibited an absorption (λmax=549 nm) derived from a reduced form of Exemplified Compound A-39. When-0.5 V was applied, the element achromatized, thus reversibly coloring and achromatizing. FIG. 8 illustrates UV-visible absorption spectra of the element fabricated in Example 12.

Examples 13 and 14, Comparative Example

Reduction Potential Measurement of EC Elements

An electrolyte, tetrabutylammonium perchlorate, was dissolved to 0.1 M in propylene carbonate, and Exemplified Compound A-13 prepared in Example 2 was subsequently dissolved to 40.0 mM to yield an EC solution of Example 13. Also, an EC solution of Example 14 was prepared in the same manner as in Example 13, except for using Exemplified Compound A-16 instead of Exemplified compound A-13, which was used in Example 13. An EC solution of the Comparative Example was prepared in the same manner as Example 13, except for using Compound 1-a instead of Exemplified compound A-13, which was used in Example 13.

The reduction potential of the EC solutions was measured with an electrochemical analyzer Model 832B, manufactured by BAS Inc. The measurement used carbon as the working electrode, platinum as the counter electrode, and $Ag/Ag^+$ electrode (solution of silver hexafluorophosphate in propylene carbonate) as the reference electrode, and also used ferrocene as the internal standard.

TABLE 2

| | Structural formula | Reduction potential |
|---|---|---|
| Example 13 | 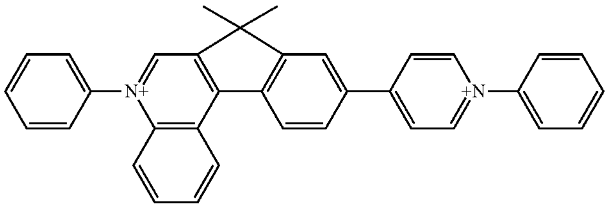 $2PF_6^-$ A-13 | −1.00 V |
| Example 14 | 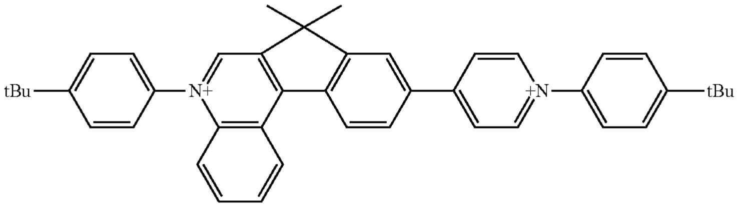 $2(CF_3SO_2)_2N^-$ A-16 | −0.99 V |
| Comparative Example | 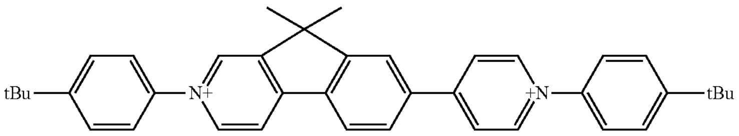 $2PF_6^-$ Compound 1-a | −1.10 V |

As presented in Table 2, Compound 1-a, which is an organic compound disclosed in PTL 1, exhibited a reduction potential of −1.10 V, whereas the organic compounds disclosed herein, Exemplified Compounds A-13 and A-16, exhibited reduction potentials of −1.00 V and −0.99 V, respectively. Thus, the organic compound according to the present disclosure exhibits a smaller reduction potential.

Accordingly, the organic compound according to the present disclosure can absorb light with wavelengths at around 550 nm.

Also, the organic compound according to the present disclosure exhibits a smaller reduction potential.

The present disclosure provides an organic compound that can absorb longer wavelength light.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2023-023495 filed Feb. 17, 2023 and No. 2023-183964 filed Oct. 26, 2023, which are hereby incorporated by reference herein in their entirety.

What is claimed is:

1. An organic compound represented by formula (1):

(1)

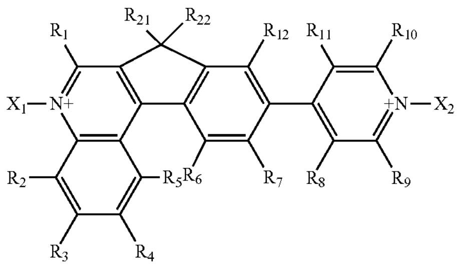

wherein $X_1$ and $X_2$ are each selected from the group consisting of substituted or unsubstituted alkyl groups, substituted or unsubstituted aryl groups, and substituted or unsubstituted aralkyl groups;

$R_1$ to $R_{12}$ are each independently selected from the group consisting of a hydrogen atom, a deuterium atom, halogen atoms, substituted or unsubstituted alkyl groups, substituted or unsubstituted alkoxy groups, and substituted or unsubstituted aryl groups; and $R_{21}$ and $R_{22}$ are each independently selected from the group consisting of a hydrogen atom, a deuterium atom, substituted or unsubstituted alkyl groups, and substituted or unsubstituted aryl groups.

2. The organic compound according to claim 1, wherein the organic compound contains monovalent anions $A_1^-$ and $A_2^-$ as counter ions.

3. The organic compound according to claim 2, wherein $A_1^-$ and $A_2^-$ are each independently selected from the group consisting of $Cl^-$, $Br^-$, $I^-$, $BF_4^-$, $PF_6^-$, $ClO_4^-$, $CF_3SO_3^-$, and $(CF_3SO_2)_2N^-$.

4. The organic compound according to claim 2, wherein $A_1^-$ and $A_2^-$ are the same anion.

5. The organic compound according to claim 1, wherein in formula (1), $X_1$ and $X_2$ are each independently selected from the group consisting of alkyl groups with 1 to 8 carbon atoms, aryl groups with 6 to 10 carbon atoms, and aralkyl groups with 6 to 10 carbon atoms.

6. The organic compound according to claim 1, wherein in formula (1), $X_1$ and $X_2$ are phenyl groups.

7. The organic compound according to claim 1, wherein in formula (1), $X_1$ and $X_2$ have the same structure.

8. The organic compound according to claim 1, wherein in formula (1), $R_1$ to $R_{12}$ are each independently selected from the group consisting of a hydrogen atom, halogen atoms, aryl groups with 6 to 10 carbon atoms, and alkoxy groups with 1 to 4 carbon atoms.

9. The organic compound according to claim 1, wherein in formula (1), $R_1$ to $R_{12}$ are hydrogen atoms.

10. An electrochromic element: comprising a pair of electrodes; and an electrochromic layer disposed between the pair of electrodes, wherein the electrochromic layer contains a first organic compound that is the organic compound as set forth in claim 1.

11. The electrochromic element according to claim 10, wherein the electrochromic layer further contains a second organic compound different from the first organic compound.

12. The electrochromic element according to claim 11, wherein the second organic compound is selected from the group consisting of phenazine-based compounds, metallocene compounds, phenylenediamine-based compounds, and pyrazoline-based compounds.

13. The electrochromic element according to claim 10, wherein the electrochromic layer further contains an electrolyte.

14. The electrochromic element according to claim 10, wherein the electrochromic layer further contains a thickener.

15. An optical filter comprising:

the electrochromic element as set forth in claim 10; and an active element connected to the electrochromic element.

16. The optical filter according to claim 15, wherein the active element drives the electrochromic element, thereby adjusting the amount of light passing through the electrochromic element.

17. A lens unit comprising:

the optical filter as set forth in claim 15; and an imaging optical system including a lens.

18. An imaging device comprising:

the optical filter as set forth in claim 15; and an imaging element configured to receive light passing through the optical filter.

19. A window comprising:

a pair of substrates;

the electrochromic element as set forth in claim 10, the electrochromic element being disposed between the pair of substrates; and an active element connected to the electrochromic element.

20. An electrochromic mirror comprising:

the electrochromic element as set forth in claim 10;

an active element connected to the electrochromic element; and a reflection member.

* * * * *